US011389242B2

(12) United States Patent
Takata et al.

(10) Patent No.: US 11,389,242 B2
(45) Date of Patent: Jul. 19, 2022

(54) CATHETER KIT

(71) Applicant: HAMAMATSU PHOTONICS K.K., Hamamatsu (JP)

(72) Inventors: Yohei Takata, Hamamatsu (JP); Yoshiyuki Shimizu, Hamamatsu (JP); Tsuyoshi Kosugi, Hamamatsu (JP); Hiroyuki Okada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 16/613,191

(22) PCT Filed: May 15, 2018

(86) PCT No.: PCT/JP2018/018698
§ 371 (c)(1),
(2) Date: Nov. 13, 2019

(87) PCT Pub. No.: WO2018/212159
PCT Pub. Date: Nov. 22, 2018

(65) Prior Publication Data
US 2021/0052326 A1 Feb. 25, 2021

(30) Foreign Application Priority Data
May 15, 2017 (JP) .............................. JP2017-096525

(51) Int. Cl.
*A61B 18/20* (2006.01)
*A61B 18/24* (2006.01)
*A61B 18/22* (2006.01)

(52) U.S. Cl.
CPC .... *A61B 18/24* (2013.01); *A61B 2018/20357* (2017.05); *A61B 2018/2288* (2013.01)

(58) Field of Classification Search
None
See application file for complete search history.

(56) References Cited

U.S. PATENT DOCUMENTS

| 3,858,577 A | | 1/1975 | Bass et al. |
| 4,326,520 A | * | 4/1982 | Alley ................. A61M 25/0111 604/159 |
| 5,314,408 A | * | 5/1994 | Salmon ................. A61B 17/22 604/22 |
| 6,373,573 B1 | | 4/2002 | Jung et al. |

(Continued)

FOREIGN PATENT DOCUMENTS

| CN | 105874369 A | 8/2016 |
| EP | 2449959 A2 | 5/2012 |

(Continued)

OTHER PUBLICATIONS

International Preliminary Report on Patentability dated Nov. 28, 2019 for PCT/JP2018/018698.

*Primary Examiner* — Lynsey C Eiseman
(74) *Attorney, Agent, or Firm* — Faegre Drinker Biddle & Reath LLP

(57) ABSTRACT

A catheter kit includes a catheter having an optical fiber, and a catheter accommodating tool which accommodates the catheter. The catheter accommodating tool has a tubular hoop, and a protection cap which is provided to the hoop. The protection cap has a transmission window through which laser light L output from the catheter passes.

7 Claims, 17 Drawing Sheets

(56) References Cited

U.S. PATENT DOCUMENTS

| | | | |
|---|---|---|---|
| 2008/0292255 A1* | 11/2008 | Stevens | G02B 6/06 385/117 |
| 2014/0236088 A1* | 8/2014 | Al-Rashdan | A61M 25/0606 604/164.03 |
| 2015/0057648 A1 | 2/2015 | Swift et al. | |
| 2016/0184022 A1 | 6/2016 | Grace et al. | |

FOREIGN PATENT DOCUMENTS

| | | |
|---|---|---|
| JP | H06-42182 Y2 | 11/1994 |
| JP | H08-262278 A | 10/1996 |
| JP | 4409499 B2 | 2/2010 |
| WO | WO 90/011722 A1 | 10/1990 |
| WO | WO-98/04321 A1 | 2/1998 |
| WO | WO 2018/012280 A1 | 1/2018 |

\* cited by examiner (a)

(b)

(a)

(b)

(c)

(a)

(b)

(a)

(b)

(a)

(b)

(c)

(a)

(b)

(a)

(b)

(a)

(b)

(c)

(a)

(b)

(a)

(b)

(a)

(b)

(c)

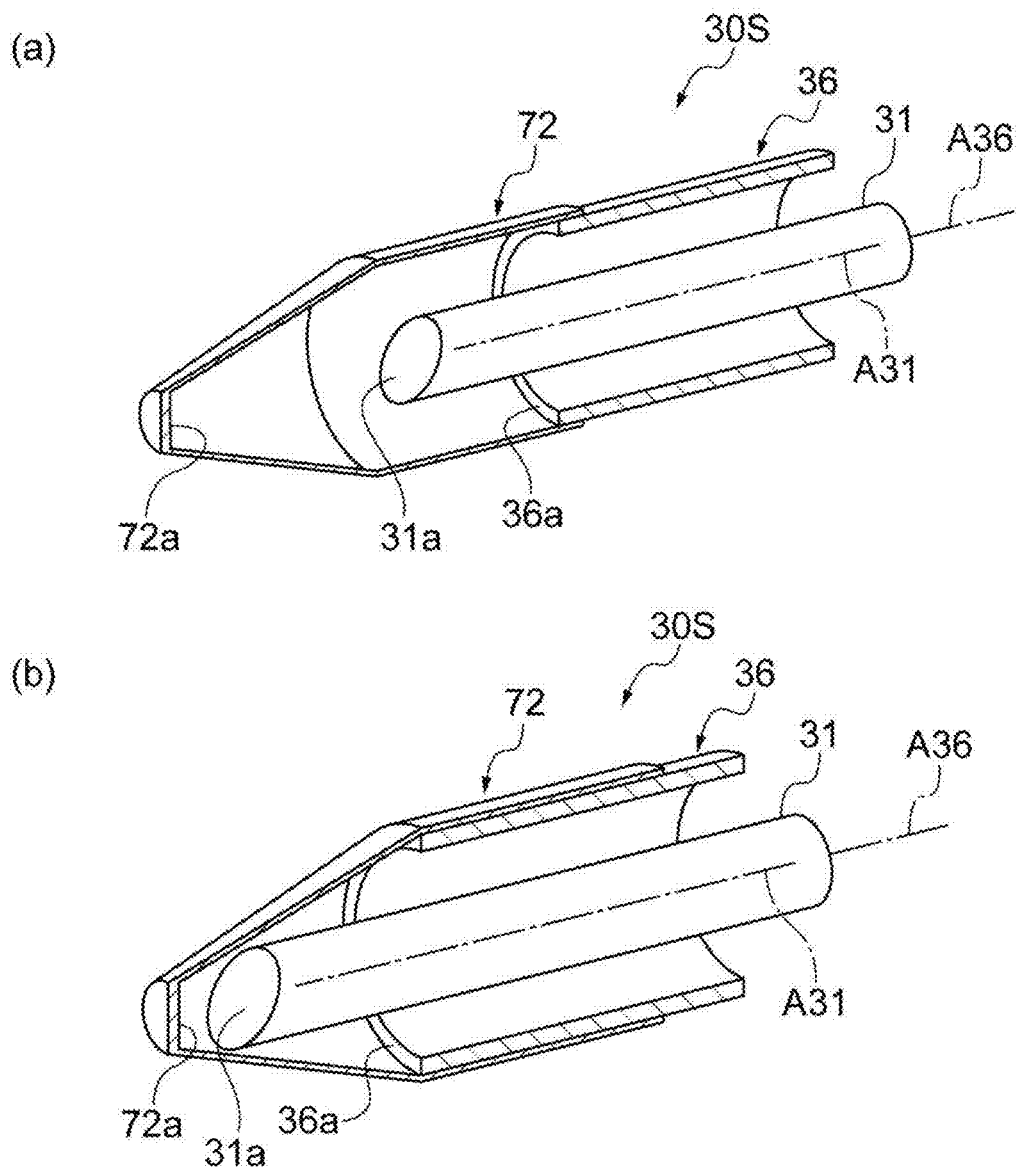

CATHETER KIT

TECHNICAL FIELD

The present invention relates to a catheter kit which accommodates a catheter with a built-in optical fiber.

BACKGROUND ART

A catheter with a built-in optical fiber is used for patient diagnosis and treatment. For example, Patent Document 1 discloses this in thrombolytic therapy. When a catheter is used for thrombolytic therapy, the catheter is first inserted into a patient's body. Thereafter, an affected area is irradiated with laser light through the catheter.

CITATION LIST

Patent Literature

[Patent Literature 1] Japanese Patent No. 4409499
[Patent Literature 2] Japanese Examined Utility Model Publication No. H6-42182
[Patent Literature 3] Japanese Unexamined Patent Publication No. H8-262278

SUMMARY OF INVENTION

Technical Problem

The catheter is inserted into a body at the time of use. Therefore, when the catheter is inserted into the body, it is required to be sufficiently sterilized. Therefore, during storage and transportation, the catheter is accommodated in a tubular container called a hoop to maintain cleanliness. Thus, in order to maintain the cleanliness of the catheter, it is desirable to store the catheter in the hoop until immediately before use.

In a method disclosed in Patent Document 1, it is desirable to irradiate an affected area with laser light having a predetermined intensity. Therefore, as disclosed in Patent Documents 2 and 3, a light intensity confirmation operation is performed immediately before start of a treatment.

Therefore, an object of the present invention is to provide a catheter kit allowing a light intensity confirmation operation to be performed easily while maintaining cleanliness of a catheter.

Solution to Problem

A catheter kit according to one aspect of the present invention includes a catheter having an optical fiber, and a catheter accommodating tool which accommodates the catheter, wherein the catheter accommodating tool includes a tubular hoop, and a closing part provided at an end portion of the hoop, and the closing part has a transmission window which transmits light emitted from the catheter.

In the catheter kit, the end portion of the hoop which accommodates the catheter is closed by the closing part. Thus, a tip end of the catheter can be protected. Furthermore, the transmission window is provided at the closing part. Therefore, the light provided from the optical fiber can be obtained in a state in which the catheter is accommodated in the hoop without taking out the catheter from the hoop. Thus, cleanliness of the catheter can be maintained, and a light intensity confirmation operation can be easily performed.

The end portion of the hoop may have an opening, a catheter tip end portion from which light transmitted through the optical fiber is emitted may be provided at the end portion of the hoop, and the transmission window may close the opening and may transmit the light. According to such a configuration, it is possible to measure the light intensity in the state in which the catheter is accommodated in the hoop. Therefore, the cleanliness of the catheter can be maintained, and the light intensity confirmation operation can be easily performed.

The closing part may be a cap member which is detachably mounted on the hoop. According to such a configuration, the configuration of the hoop end portion can be selected according to the form of measurement of the light intensity. That is, it is possible to select a mode in which the measurement is performed while the end from which light is emitted is protected, and a mode in which the measurement is performed while light is directly incident on a measurement device.

The closing part may be a cover part which is a part of the hoop and is integrated with the hoop. According to such a configuration, the cover part is not separated from the hoop. Therefore, the tip end portion of the catheter can be protected reliably.

The hoop may have a through hole which extends in a direction intersecting a longitudinal direction of the hoop and extends from an outer circumferential surface to an inner circumferential surface. According to such a configuration, a sterilization gas can be appropriately provided to the catheter accommodated in the hoop.

The catheter accommodating tool may further include a position adjustment part provided at the hoop, the hoop may include a hoop tip end portion which is the end portion, and a hoop base end portion which is opposite to the tip end portion, and the position adjustment part may change a position of the catheter tip end portion from which the light transmitted through the optical fiber with respect to the hoop tip end portion is emitted. According to such a configuration, it is possible to change the position of the catheter tip end portion at the time of storage and measurement. That is, at the time of storage, it is possible to dispose the catheter tip end portion inside from the hoop tip end portion. As a result, the catheter tip end portion can be protected. Furthermore, at the time of measurement, it is possible to align the catheter tip end portion with the hoop tip end portion. As a result, it is possible to curb occurrence of variation in a distance from the catheter tip end portion to a light receiving part.

Advantageous Effects of Invention

According to the present invention, a catheter kit capable of maintaining cleanliness of a catheter and allowing a light intensity confirmation operation to be performed easily is provided.

BRIEF DESCRIPTION OF DRAWINGS

FIG. 17 is a perspective view showing a cross section of a catheter kit according to a ninth modified example.

DESCRIPTION OF EMBODIMENTS

Hereinafter, embodiments of the present invention will be described in detail with reference to the attached drawings. In the description of the drawings, the same elements will be designated by the same reference symbols, and duplicate descriptions will be omitted.

First Embodiment

Figure 1:
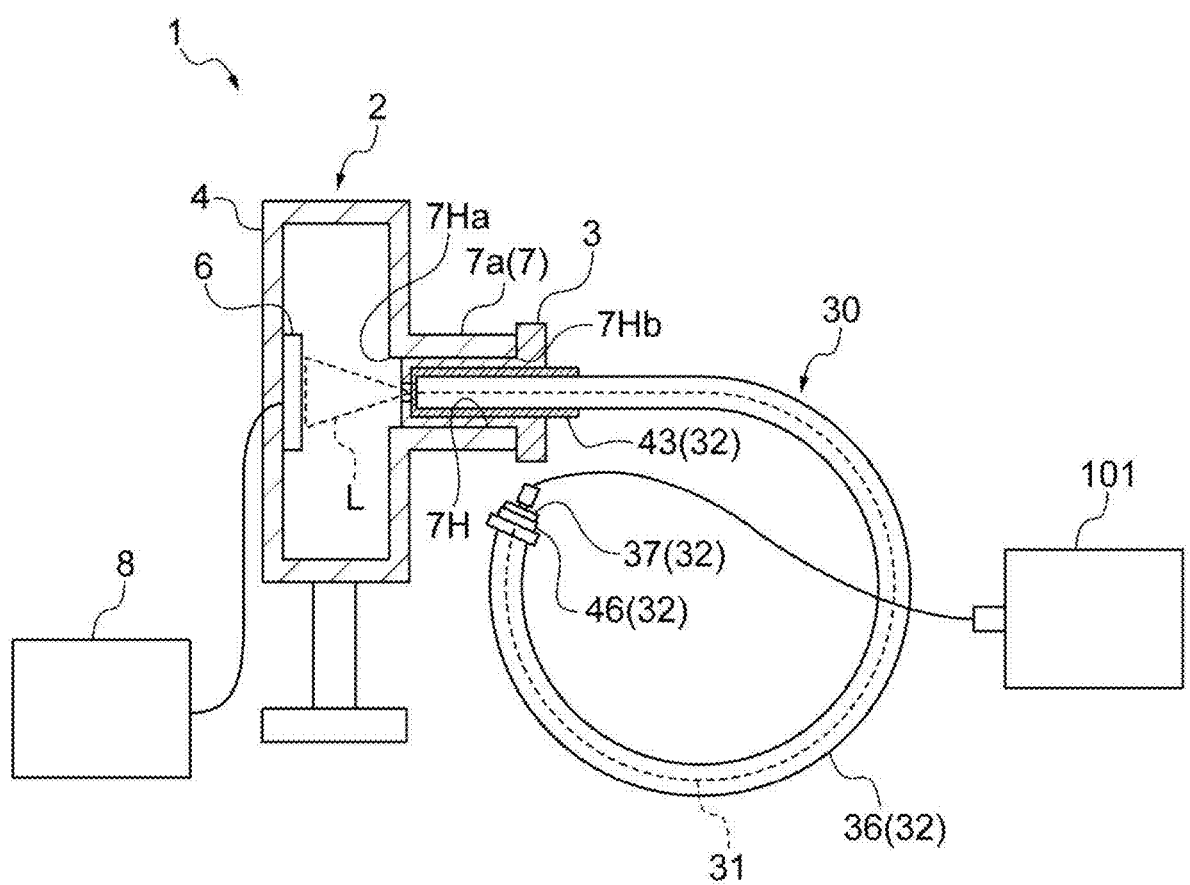
FIG. 1 is a view showing a configuration of a light measurement device according to a first embodiment.

As shown in FIG. 1, a light measurement device 1 measures an intensity of laser light L. The laser light L is provided from a light source 101 to a catheter kit 30. Then, the laser light L is emitted from the catheter kit 30. The light measurement device 1 includes a power meter 2 and an adapter 3 (a second adapter). In the following description, the side of the respective elements from which light is emitted is referred to as a "tip end." The side opposite to the "tip end" is referred to as a "base end." For example, in the catheter kit 30, an end portion which emits the laser light L is a "tip end portion." An end portion which receives the laser light L is a "base end portion."

The power meter 2 includes a case body 4, a light receiving part 6, a mounting part 7, and a processing device 8.

The case body 4 holds a relative positional relationship between the light receiving part 6 and the mounting part 7. The case body 4 is formed of an opaque material. The case body 4 and the adapter 3 constitute a closed space. The light receiving part 6 is disposed inside the closed space. According to such a configuration, it is possible to prevent stray light from being incident on the light receiving part 6.

The light receiving part 6 receives the laser light L output from the catheter kit 30. The light receiving part 6 includes, for example, a light absorber. The light receiving part 6 converts absorbed light into heat. Thereafter, the light receiving part 6 outputs a change of heat as a change in an electrical signal. For example, the light absorber may include 3A-P manufactured by Ophir, and the like. The electrical signal output from the light receiving part 6 is transmitted to the processing device 8 via a signal cable. The processing device 8 obtains the intensity of the light received by the light receiving part 6 on the basis of the electrical signal. Then, the processing device 8 displays an intensity value thereof.

The mounting part 7 is provided at a position facing the light receiving part 6. The mounting part 7 may be part of the case body 4. The mounting part 7 defines a position of the catheter kit 30 with respect to the light receiving part 6. The position of the catheter kit 30 with respect to the light receiving part 6 includes a distance from a tip end portion of the catheter kit 30 to the light receiving part 6 in a traveling direction of the laser light L emitted from the catheter kit 30. Furthermore, the position includes a position of the tip end portion of the catheter kit 30 with respect to the light receiving part 6 in a plane orthogonal to the traveling direction of the laser light L. The mounting part 7 has a standing tubular part 7a which protrudes from the case body 4. Furthermore, the standing tubular part 7a has an adapter arrangement part 7H which is a through hole. The catheter kit 30 is disposed in the adapter arrangement part 7H via the adapter 3. A tip end of the adapter arrangement part 7H is a tip end opening 7Ha provided in an inner wall of the case body 4. A base end of the adapter arrangement part 7H is a base end opening 7Hb provided in an end portion of the mounting part 7.

Figure 2:
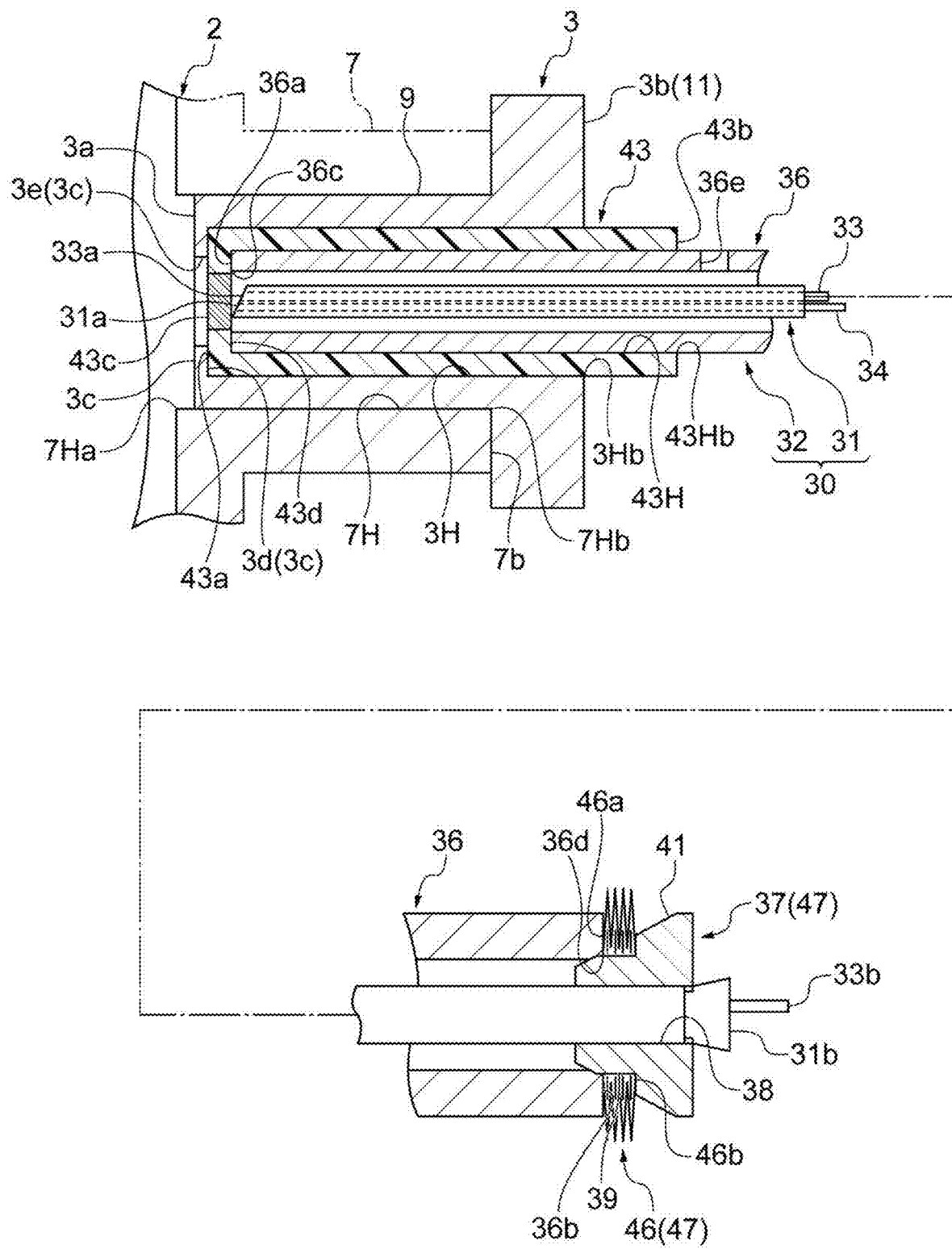
FIG. 2 is an enlarged cross-sectional view showing a configuration of an adapter and a catheter kit shown in FIG. 1.

As shown in FIG. 2, the adapter 3 allows the catheter kit 30 to be mounted in the power meter 2. The adapter 3 may be formed of, for example, polyacetal. The adapter 3 has an adapter main body 9 and an adapter flange 11. The adapter main body 9 and the adapter flange 11 are integrally formed. The adapter main body 9 is disposed in the adapter arrangement part 7H. The adapter main body 9 has an adapter tip end surface 3a. A male thread may be provided on an outer circumferential surface of the adapter main body 9. The adapter flange 11 is provided on the base end side. The adapter flange 11 has an adapter base end surface 3b. An outer diameter of the adapter flange 11 is larger than an inner diameter of the adapter arrangement part 7H. The adapter flange 11 may be in contact with a mounting end surface 7b of the mounting part 7.

The adapter 3 has a hoop arrangement part 3H which holds a tip end of the catheter kit 30. The hoop arrangement part 3H is a hole which extends from the adapter base end surface 3b toward the adapter tip end surface 3a. Also, the base end side of the hoop arrangement part 3H is a base end opening 3Hb provided in the adapter base end surface 3b. The base end opening 3Hb may be chamfered (tapered). An adapter tip end wall 3d is provided on the tip end side of the hoop arrangement part 3H. When the catheter kit 30 is disposed in the hoop arrangement part 3H, the tip end of the catheter kit 30 is in contact with the adapter tip end wall 3d. More specifically, a tip end surface of a protection cap 43 which will be described later is in contact with the adapter tip end wall 3d. Thus, the adapter tip end wall 3d defines an insertion depth of the catheter kit 30 with respect to the adapter 3. A light passing part 3e which is a through hole is provided in the adapter tip end wall 3d. The light passing part 3e guides the laser light L emitted from the catheter kit 30 to the light receiving part 6.

Therefore, a contact part 3c (a second contact part) is constituted by the adapter tip end wall 3d and the light passing part 3e.

Next, the catheter kit 30 will be described in detail. The catheter kit 30 includes a catheter 31 and a catheter accommodating tool 32. The catheter 31 has a built-in optical fiber 33. The catheter 31 may also include other components 34 required for treatment and examination, in addition to the optical fiber 33. The optical fiber 33 has an optical fiber tip end portion 33a and an optical fiber base end portion 33b. The optical fiber tip end portion 33a is inserted into a human body. Furthermore, the optical fiber tip end portion 33a emits the laser light L. The light source 101 (refer to FIG. 1) is connected to the optical fiber base end portion 33b. Additionally, the laser light L is provided to the optical fiber base end portion 33b.

The catheter accommodating tool 32 accommodates the catheter 31. The catheter accommodating tool 32 includes a hoop 36, a holding plug 37 (a catheter holding part), the protection cap 43 (a closing part, a cap member), and a bellows 46 (refer to FIG. 1).

The hoop 36 has a tubular pipe shape. The hoop 36 described in the embodiment is used at a medical site. The hoop 36 refers to a resin tube into which the catheter 31 is inserted. The hoop 36 does not have to be flexible. The hoop 36 may be flexible or non-flexible. The hoop 36 includes a hoop tip end portion 36a in which a catheter tip end portion 31a is disposed, and a hoop base end portion 36b in which the catheter base end portion 31b side is disposed. A tip end opening 36c is provided in the hoop tip end portion 36a. That is, the hoop tip end portion 36a is not closed. In other words, the hoop tip end portion 36a is open. The hoop base end portion 36b also has a base end opening 36d. That is, the hoop base end portion 36b is also not closed. In other words, the hoop base end portion 36b is open. A gas introduction hole 36e is provided in the hoop 36. The gas introduction hole 36e is provided in a side wall of the hoop 36. Additionally, the gas introduction hole 36e passes therethrough from an outer circumferential surface to an inner circumferential surface.

Here, a relationship between an inner diameter (f) and an outer diameter (d) of the hoop 36 and an inner diameter (e) of the light passing part 3e of the adapter 3 is $f<e<d$. According to this dimensional relationship, it is possible to prevent the catheter tip end portion 31a from coming into contact with an unsterilized portion.

The holding plug 37 is disposed to be press-fitted into the base end opening 36d on the side of the hoop base end portion 36b. The holding plug 37 includes a catheter arrangement part 38, a press-fit part 39 which is press-fitted into the hoop 36, and a flange part 41. The catheter arrangement part 38 is a through hole which holds the catheter 31. The holding plug 37 holds the position of the catheter 31 with respect to the hoop 36 when inserted into the hoop 36. That is, the holding plug 37 is fixed to the hoop 36. Additionally, the holding plug 37 holds the catheter 31. Thus, the holding plug 37 inserted into the hoop 36 holds the position of the catheter 31 with respect to the hoop 36.

The catheter arrangement part 38 is disposed on the side of the catheter base end portion 31b. An inner diameter of the catheter arrangement part 38 is slightly smaller than an outer diameter of the catheter 31. According to such a configuration, an inner circumferential surface of the catheter arrangement part 38 is press-fitted onto an outer circumferential surface of the catheter 31. As a result, the position of the catheter 31 with respect to the holding plug 37 is held. The press-fit part 39 is press-fitted into the hoop 36 from the base end opening 36d of the hoop base end portion 36b. An outer diameter of the press-fit part 39 is slightly larger than an inner diameter of the hoop 36. According to such a configuration, an outer circumferential surface of the press-fit part 39 is press-fitted into an inner circumferential surface of the hoop 36. As a result, a position of the holding plug 37 with respect to the hoop 36 is held. The flange part 41 is provided on the base end side of the press-fit part 39. An outer diameter of the flange part 41 is larger than an inner diameter of the hoop 36.

The protection cap 43 is mounted on the hoop 36. The protection cap 43 has a tubular shape of which one end is closed and the other end is open. The protection cap 43 may be formed of, for example, acrylic. The protection cap 43 closes the tip end opening 36c of the hoop tip end portion 36a. According to such a configuration, the catheter tip end portion 31a is protected. Further, the protection cap 43 transmits the laser light L emitted from the catheter tip end portion 31a. The protection cap 43 has a cap tip end portion 43a and a cap base end portion 43b. The cap tip end portion 43a has a transmission window 43c. The transmission window 43c closes the tip end opening 36c. Furthermore, the transmission window 43c transmits the laser light L. The cap base end portion 43b has a base end opening 43Hb of the hoop arrangement part 43H into which the hoop 36 can be inserted.

The bellows 46 is disposed between the hoop 36 and the holding plug 37. The bellows 46 which is a so-called bellows tube can extend and contract in an axial direction thereof. The bellows 46 has an elasticity to maintain a predetermined length when no external force is applied. For example, when the bellows 46 is pressed in the axial direction, a length of the bellows 46 is reduced. On the other hand, when the pressing is stopped, the length of the bellows 46 returns to the length before the pressing.

Figure 3:
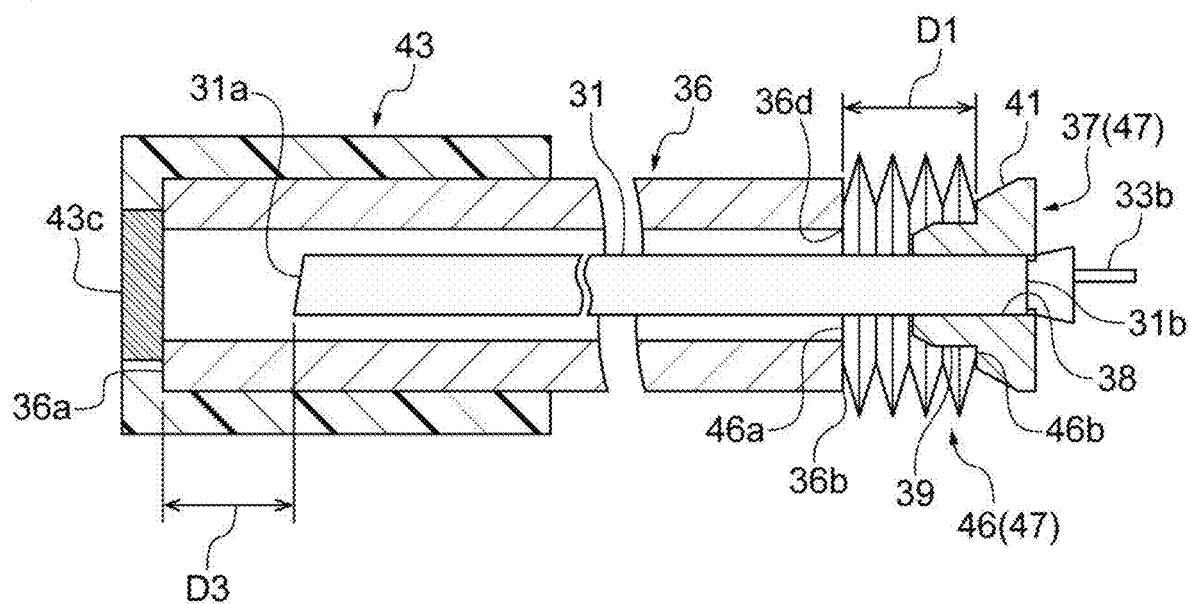
FIG. 3 is a cross-sectional view for explaining an operation of a position adjustment mechanism.
Figure 3:
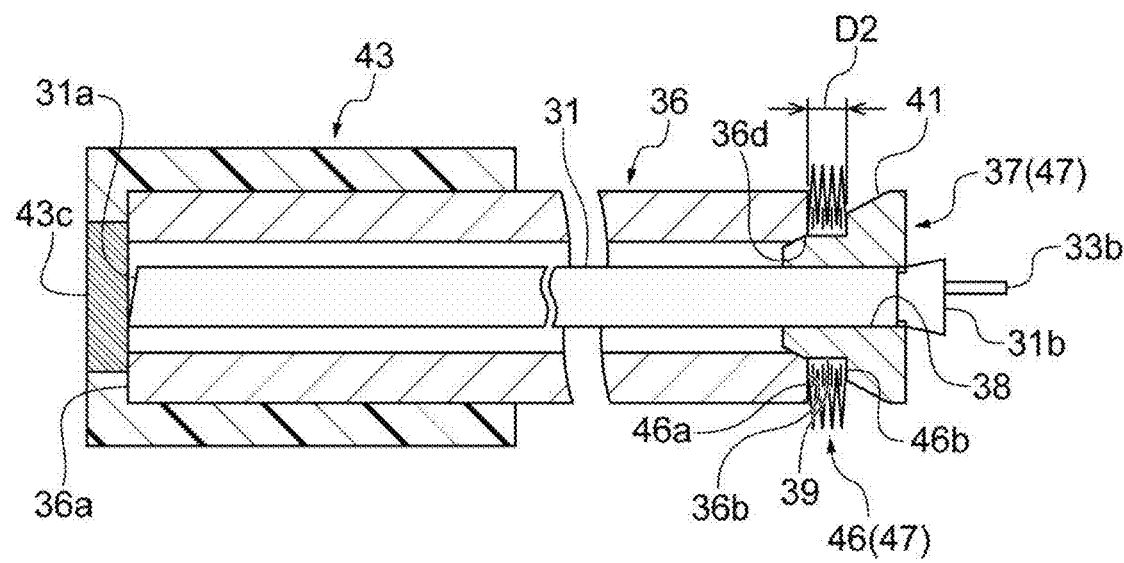

The bellows 46 has a bellows tip end portion 46a and a bellows base end portion 46b. The bellows tip end portion 46a is in contact with the hoop base end portion 36b. The bellows base end portion 46b is in contact with the flange part 41 of the holding plug 37. According to such a configuration, a constant gap is maintained between a base end surface of the hoop base end portion 36b and an end surface of the flange part 41 of the holding plug 37 (refer to a gap D1 in FIG. 3(a)). On the other hand, it is assumed that the holding plug 37 is pushed to the hoop 36 side and the press-fit part 39 of the holding plug 37 is pressed into the hoop 36. Also in this case, a restoring force of the bellows 46 is generated. However, the restoring force is smaller than a frictional force between the press-fit part 39 and the inner circumferential surface of the hoop 36. Accordingly, a state in which the holding plug 37 is pushed to the hoop 36 side is maintained (refer to a gap D2 in FIG. 3(b)). The bellows 46 may not generate the restoring force. In this case, the bellows 46 can maintain a stretched state (that is, a state of FIG. 3(a)) and a contracted state (a state of FIG. 3(b)) without requiring additional components.

That is, with the bellows 46 and the holding plug 37, the position of the catheter 31 with respect to the hoop 36 can be switched to a first position or a second position. Therefore, the bellows 46 and the holding plug 37 constitute a position adjustment mechanism 47 (a position adjusting part). First, when the holding plug 37 is in a state in which it is not pushed into the hoop 36, the catheter 31 is held at the first position. In the first position, the catheter tip end portion 31a is disposed closer to the base end from the hoop tip end portion 36a (refer to FIG. 3(a)). Here, a gap from a tip end surface of the hoop tip end portion 36a to a tip end surface of the catheter tip end portion 31a is D3. The gap D3 is obtained by subtracting the gap D2 from the gap D1 (D3=D1−D2). On the other hand, when the holding plug 37 is in a state in which it is pushed into the hoop 36, the catheter 31 is held at the second position. In this second position, the positions of the hoop tip end portion 36a and the catheter tip end portion 31a coincide with each other (refer to FIG. 3(*b*)).

Figure 4:
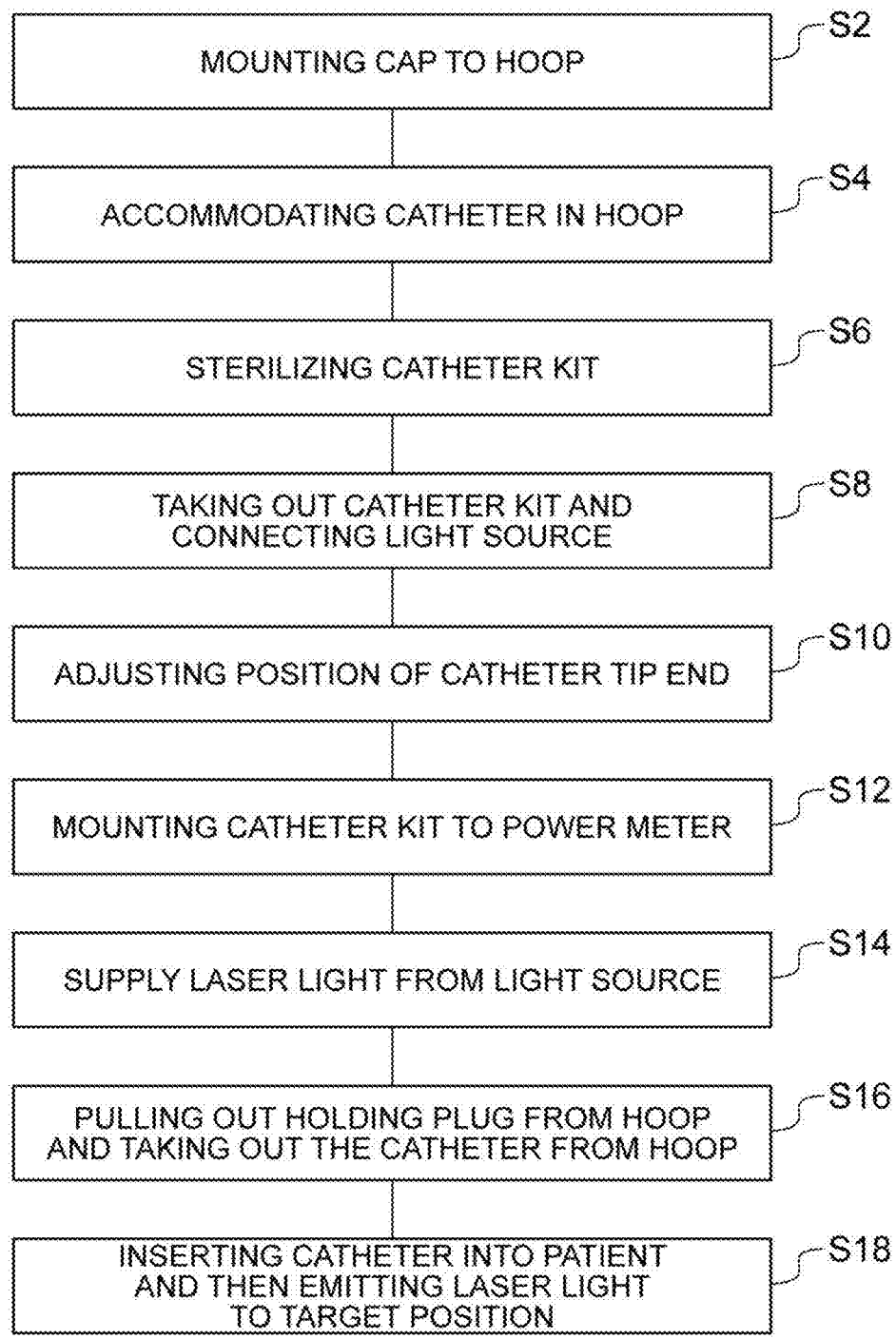
FIG. 4 is a flowchart showing a main process of a light measurement method according to the first embodiment.

Next, a light intensity measurement method using the light measurement device 1 will be described with reference to a flowchart shown in FIG. 4. First, a process of preparing the catheter kit 30 will be described.

Figure 5:
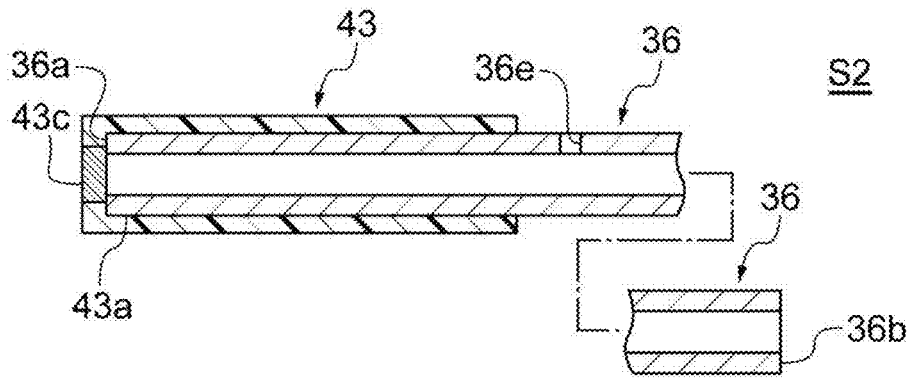
FIG. 5 is a view for explaining the main process shown in FIG. 4.
Figure 5:
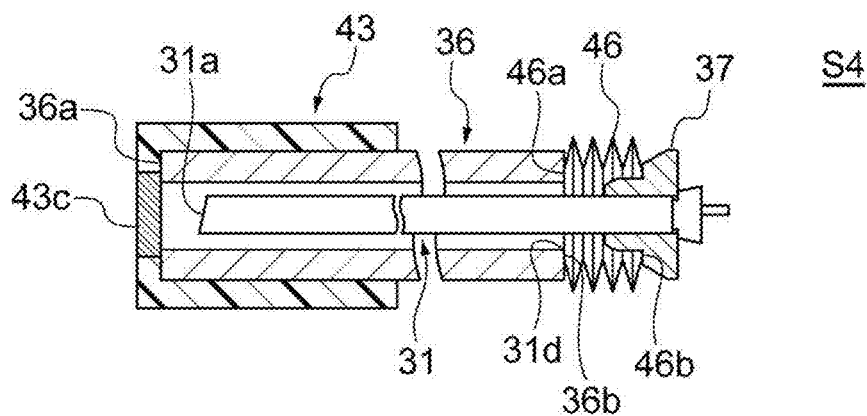
Figure 5:
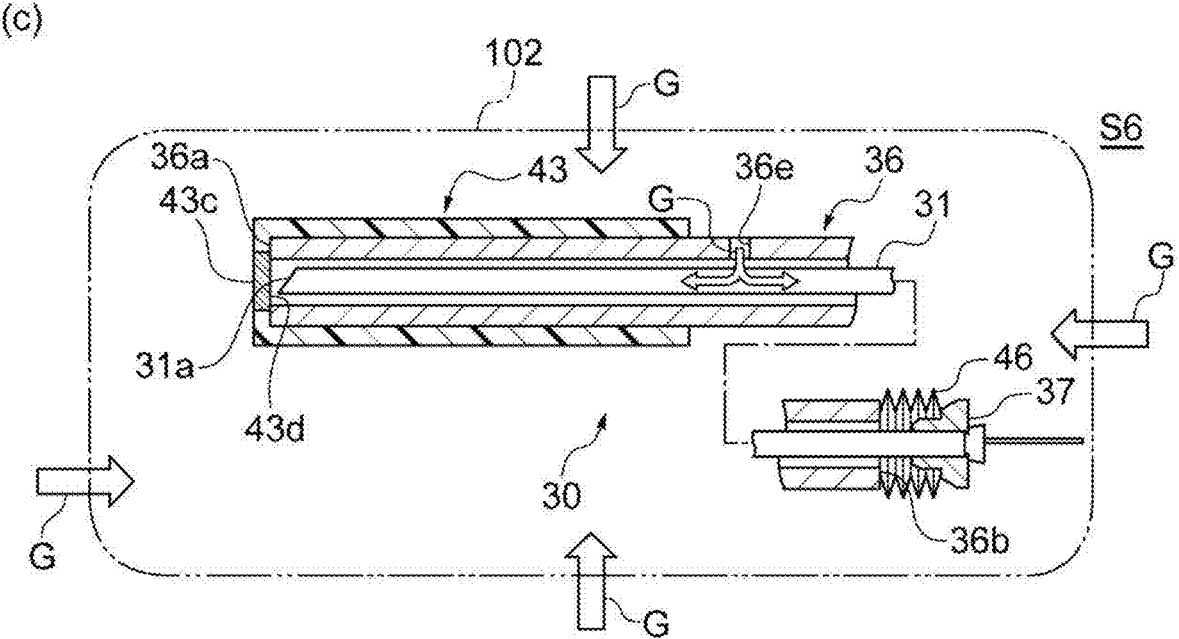

Step S2 is carried out (refer to FIG. 5(*a*)). First, the protection cap 43 is mounted on the hoop 36. In Step S2, the protection cap 43 is completely covered on the hoop 36. In other words, the tip end surface of the hoop tip end portion 36a is brought into contact with an inner surface of the cap tip end portion 43a. Also, in Step S2, a gap may be provided between the tip end surface of the hoop tip end portion 36a and the inner surface of the cap tip end portion 43a.

Next, Step S4 is performed (refer to FIG. 5(*b*)). In Step S4, the catheter 31 is accommodated in the hoop 36. Further, in Step S4, the catheter tip end portion 31a does not coincide with the hoop tip end portion 36a. That is, the bellows 46 is disposed between the hoop 36 and the holding plug 37. That is, the catheter 31 is accommodated in the hoop 36 so that the catheter 31 is at the first position. Specifically, the holding plug 37 is mounted on the bellows base end portion 46b. Further, the bellows tip end portion 46a is mounted on the base end surface of the hoop base end portion 36b. Here, the bellows 46 has a predetermined length in the axial direction. The predetermined length corresponds to, for example, a distance from the tip end surface of the hoop tip end portion 36a to the tip end surface of the catheter tip end portion 31a in an accommodated state. In a procedure of performing Steps S2 and S4, Step S4 may be performed after Step S2, as described above. In addition, Step S2 may be performed after Step S4.

Next, Step S6 is performed (refer to FIG. 5(*c*)). In Step S6, the catheter kit 30 is sterilized. Specifically, first, the catheter kit 30 is put into a sterilization bag 102. Next, the sterilization bag 102 is sealed. Next, the catheter kit 30 and the sterilization bag 102 are placed inside a chamber (not shown). Next, the inside of the chamber is degassed. Next, a sterilization gas G is supplied into the chamber. The sterilization bag 102 formed so that one side surface is formed of vinyl and the other side surface is formed of a non-woven fabric. Therefore, the sterilization gas G is filled into the bag even when the sterilization bag 102 is sealed. An example of the sterilization gas G includes ethylene oxide gas (EoG). Then, the catheter kit 30 is sterilized by the sterilization gas G.

However, the catheter 31 is accommodated in the hoop 36. The hoop tip end portion 36a is closed by a protection cap 43. The hoop base end portion 36b is closed by the holding plug 37 and the bellows 46. Here, the hoop 36 has a gas introduction hole 36e. The sterilization gas G is introduced into the hoop 36 from the gas introduction hole 36e. Therefore, according to the gas introduction hole 36e, the catheter 31 accommodated in the hoop 36 can be reliably sterilized. After the sterilization gas G is filled in, the sterilization gas G is degassed from the chamber.

The catheter kit 30 which has been sterilized by Steps S2, S4 and S6 as described above is prepared.

Subsequently, a process of measuring the catheter kit 30 will be described.

Figure 6:
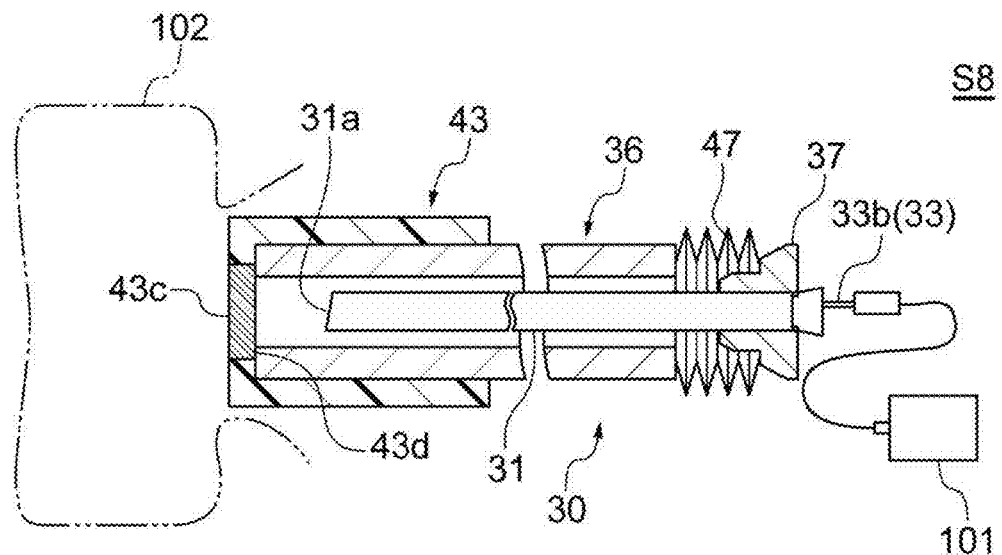
FIG. 6 is a view for explaining a main process following the process shown in FIG. 5.
Figure 6:
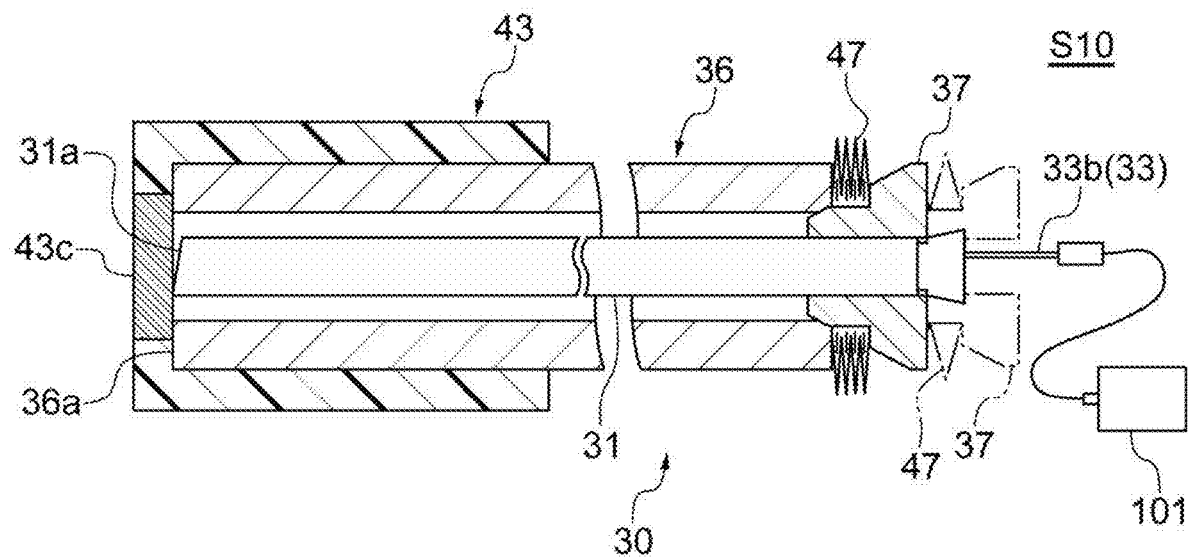

First, Step S8 is performed (refer to FIG. 6(*a*)). Specifically, the catheter kit 30 is taken out of the sterilization bag 102. Then, the light source 101 is connected to the optical fiber base end portion 33b of the optical fiber 33.

Next, Step S10 is performed (refer to FIG. 6(*b*)). In Step S10, the holding plug 37 is pushed into the hoop 36. That is, the position of the catheter tip end portion 31a coincides with the position of the hoop tip end portion 36a.

Figure 7:
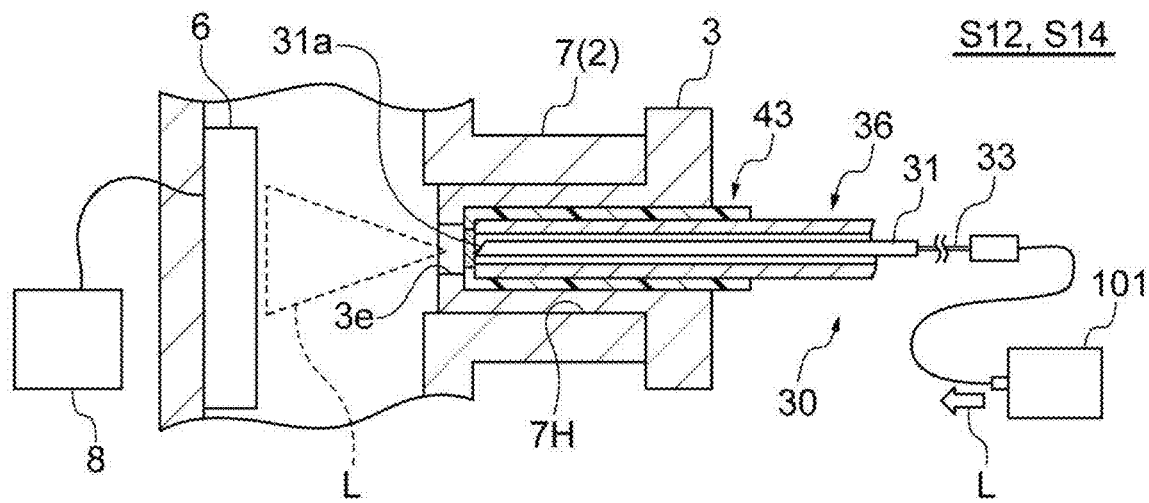
FIG. 7 is a view for explaining a main process following the process shown in FIG. 6.
Figure 7:
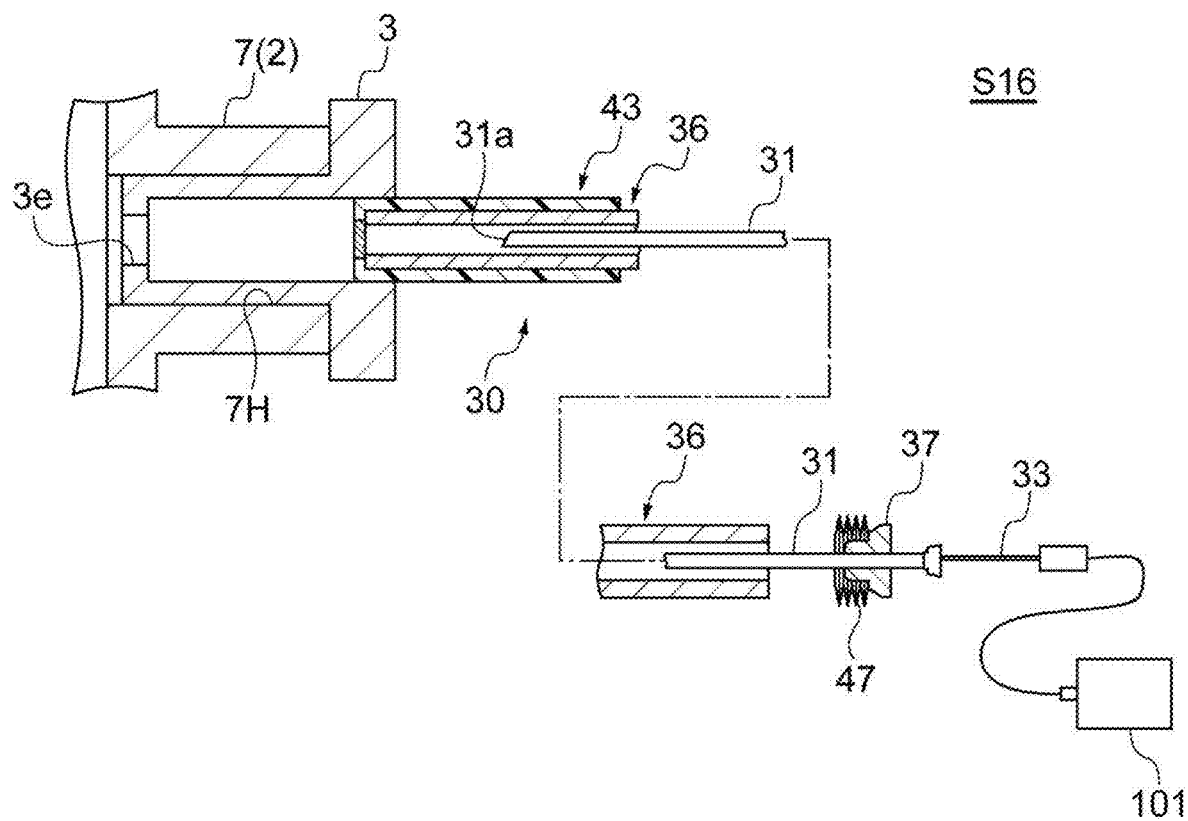

Next, Step S12 is performed (refer to FIG. 7(*a*)). First, the catheter kit 30 is mounted in the power meter 2. More specifically, the adapter 3 is screwed into the mounting part 7 of the power meter 2. Then, the tip end side (the protection cap 43 side) of the catheter kit 30 is inserted into the adapter 3.

Next, Step S14 is performed (refer to FIG. 7(*a*)). Specifically, the light source 101 is operated. As a result, the laser light L is generated. The laser light L is emitted from the catheter tip end portion 31a through the optical fiber 33. The emitted laser light L is incident on the light receiving part 6. The light receiving part 6 outputs an electrical signal according to the incident laser light L. The content of the signal is displayed on the processing device 8. It is confirmed that the predetermined intensity of the laser light L is obtained on the basis of the displayed content of the signal.

Next, Step S16 is performed (refer to FIG. 7(*b*)). Specifically, the catheter kit 30 is pulled out of the adapter 3. Next, the holding plug 37 is pulled out of the hoop 36. As a result, the catheter 31 is taken out of the hoop 36. Then, in Step S18 (not shown), a predetermined treatment or examination is performed using the catheter 31.

In the light measurement device 1 according to the first embodiment, the mounting part 7 defines the position of the hoop 36 with respect to the light receiving part 6. As a result, it is not necessary to take out the catheter 31 from the hoop 36 to measure the intensity of the laser light L. Then, it is possible to measure the intensity of the laser light L in a state in which the catheter 31 is accommodated in the hoop 36. As a result, the cleanliness of the catheter 31 can be maintained. Furthermore, the catheter 31 does not have to be taken out of the hoop 36. As a result, the process required to measure the laser light L can be simplified. Therefore, according to the light measurement device 1, the cleanliness of the catheter 31 can be maintained, and the light intensity confirmation operation can be easily performed.

In the catheter kit 30 according to the first embodiment, the position of the catheter 31 with respect to the hoop 36 is held by the holding plug 37. According to such a configuration, when the intensity of the laser light L is measured, it is possible to curb occurrence of variation of a distance from the catheter tip end portion 31a to the light receiving part 6.

Furthermore, the catheter kit 30 further includes the position adjustment mechanism 47 which is provided at the hoop base end portion 36b and changes the position of the catheter tip end portion 31a with respect to the hoop tip end portion 36a in an extending direction of the hoop 36. According to such a configuration, it is possible to switch between the position of the catheter tip end portion 31a at the time of storage and the position of the catheter tip end portion 31a at the time of measurement. That is, at the time of storage, the catheter tip end portion 31a can be disposed on the inner side of the hoop tip end portion 36a. As a result, the catheter tip end portion 31a can be protected. Furthermore, at the time of measurement, it is possible to align the catheter tip end portion 31a with the position of the hoop tip end portion 36a. As a result, it is possible to curb the occurrence of the variation in the distance from the catheter tip end portion 31a to the light receiving part 6.

The holding plug 37 of the catheter kit 30 holds the position of the catheter 31 relative to the position of the hoop 36 so that the catheter tip end portion 31a is aligned with the hoop tip end portion 36a in the extending direction of the hoop 36. According to such a configuration, the position of the hoop tip end portion 36a is defined. As a result, the position of the catheter tip end portion 31a is defined. Therefore, the occurrence of the variation in the distance from the catheter tip end portion 31a to the light receiving part 6 can be further curbed.

The catheter kit 30 further includes the protection cap 43 which is mounted on the hoop tip end portion 36a and closes the tip end opening 36c of the hoop tip end portion 36a. According to such a configuration, the catheter tip end portion 31a can be protected.

More specifically, the catheter kit 30 further includes the protection cap 43 which is mounted on the hoop 36, and the adapter 3 which disposes the hoop 36 on which the protection cap 43 is mounted to the mounting part 7. The hoop 36 has the hoop tip end portion 36a in which the catheter tip end portion 31a is disposed and which includes the tip end opening 36c. The protection cap 43 is mounted on the hoop tip end portion 36a. The protection cap 43 has the cap tip end portion 43a including the transmission window 43c which closes the tip end opening 36c and transmits the laser light L emitted from the optical fiber 33. The adapter 3 has the contact part 3c with which the cap tip end portion 43a is in contact. According to such a configuration, the protection cap 43 having the transmission window 43c is disposed between the catheter tip end portion 31a and the light receiving part 6. The transmission window 43c closes the tip end opening 36c of the hoop tip end portion 36a. Therefore, the catheter tip end portion 31a can be protected.

In the light measurement method according to the first embodiment, the position of the hoop 36 with respect to the light receiving part 6 is defined in Step S12 in which the hoop 36 is disposed in the mounting part 7. As a result, it is not necessary to take out the catheter 31 from the hoop 36 to measure the intensity of the laser light L. Then, in Step S14 in which the intensity of the laser light L is obtained, it is possible to measure the intensity of the laser light L in a state in which the catheter 31 is accommodated in the hoop 36. Therefore, the cleanliness of the catheter 31 can be maintained. Furthermore, the catheter 31 does not have to be taken out of the hoop 36. As a result, the process required to measure the laser light L can be simplified. Accordingly, according to the light measurement method, the cleanliness of the catheter 31 can be maintained, and the light intensity confirmation operation can be easily performed.

Second Embodiment

Figure 8:
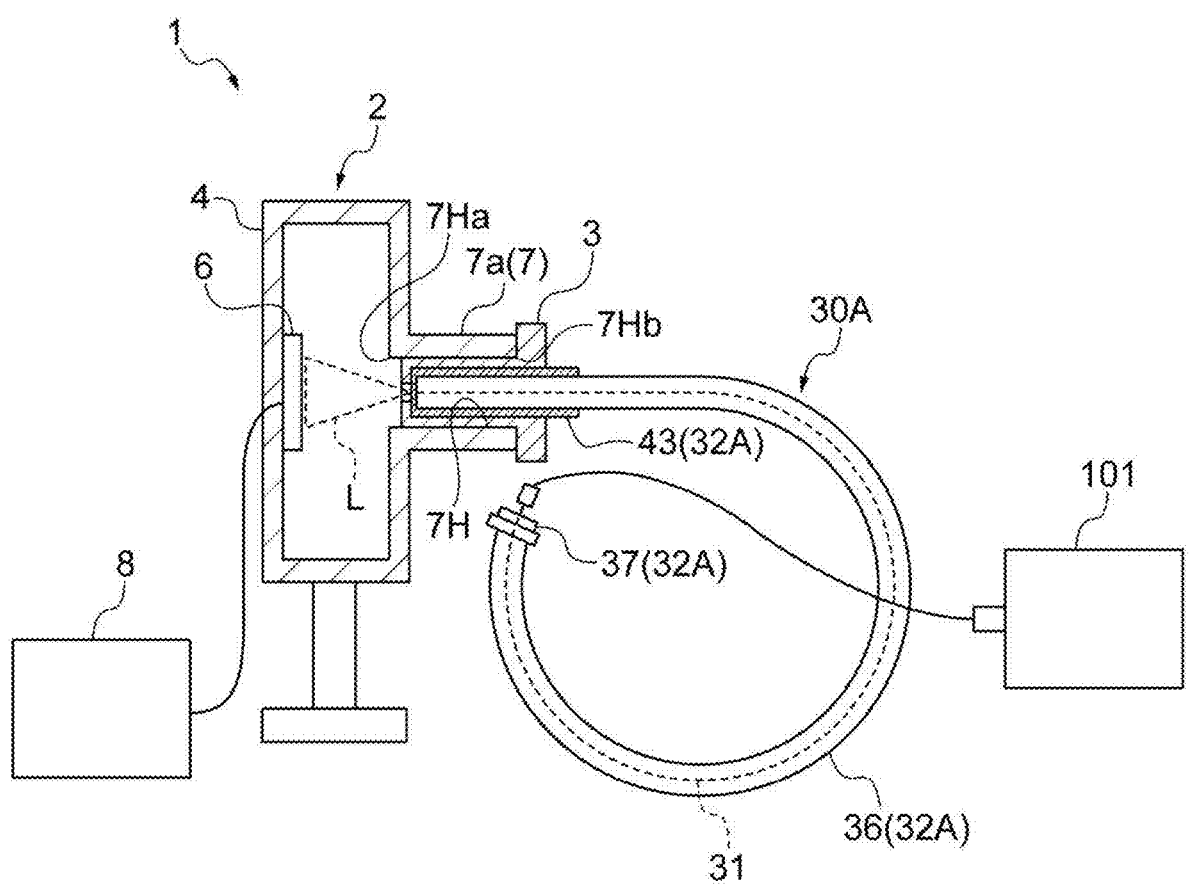
FIG. 8 is a view showing a configuration of a light measurement device according to a second embodiment.
Figure 9:
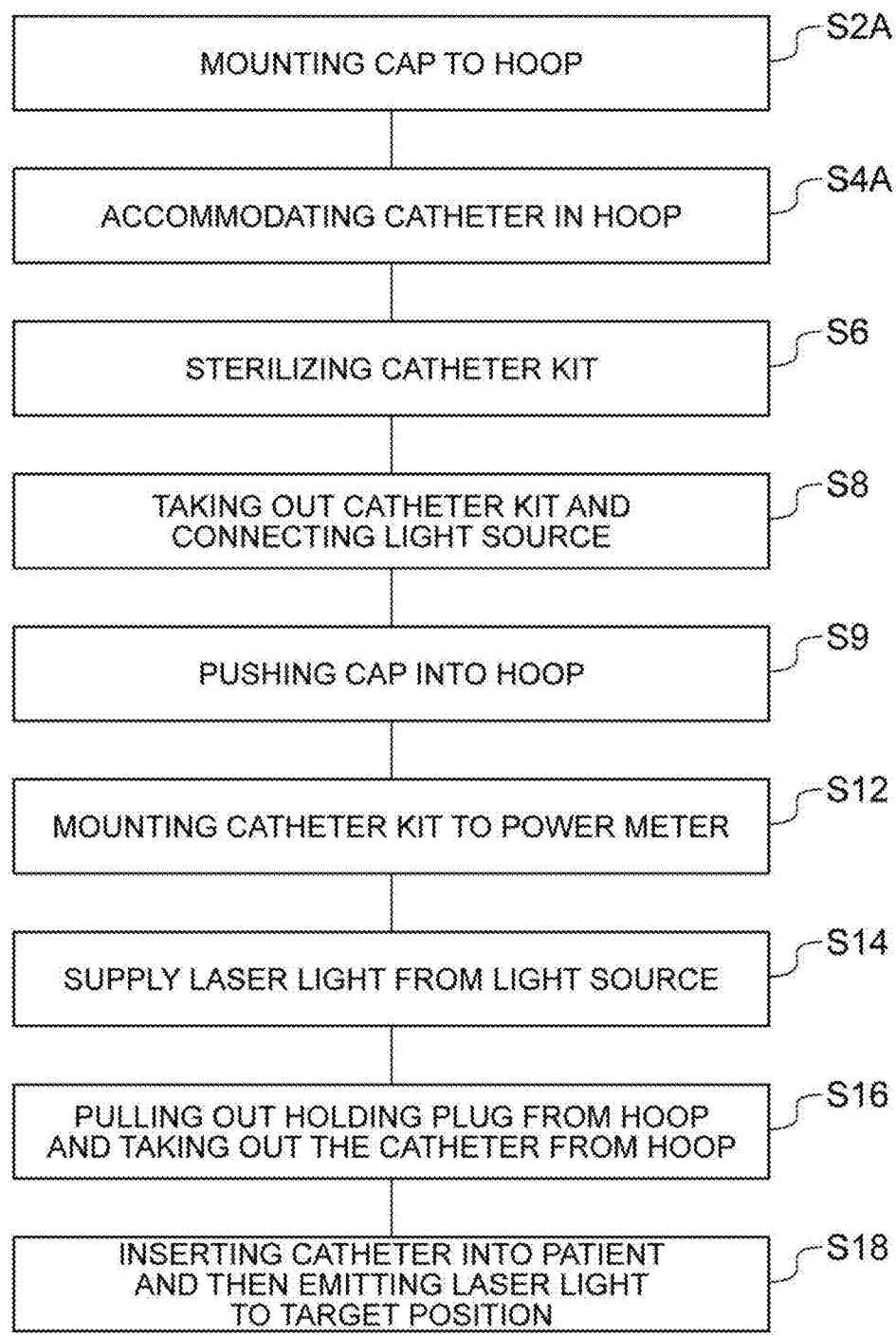
FIG. 9 is a flowchart showing a main process of a light measurement method according to the second embodiment.

A light measurement device and a catheter kit according to a second embodiment will be described. As shown in FIG. 8, the catheter kit 30A of the second embodiment is different from the catheter kit 30 of the first embodiment in that the position adjustment mechanism 47 is not provided. On the other hand, the light measurement device 1 of the second embodiment has the same configuration as that of the light measurement device 1 of the first embodiment. Hereinafter, a light measurement method using the catheter kit 30A which does not have the position adjustment mechanism 47 will be described with reference to the flowchart of FIG. 9.

Figure 10:
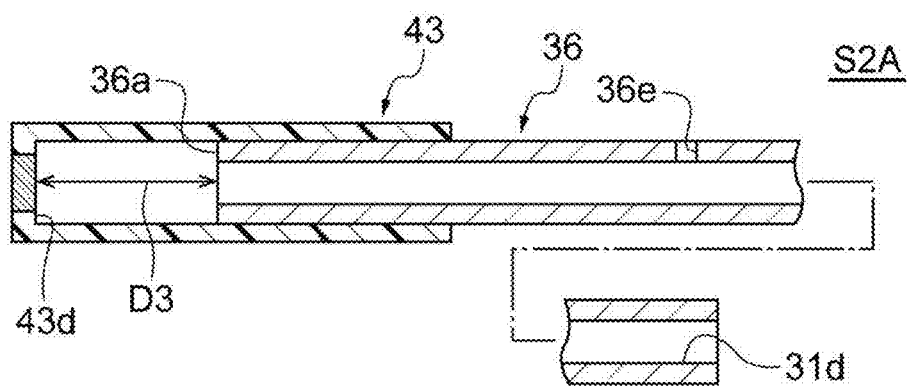
FIG. 10 is a view for explaining the main process shown in FIG. 9.
Figure 10:
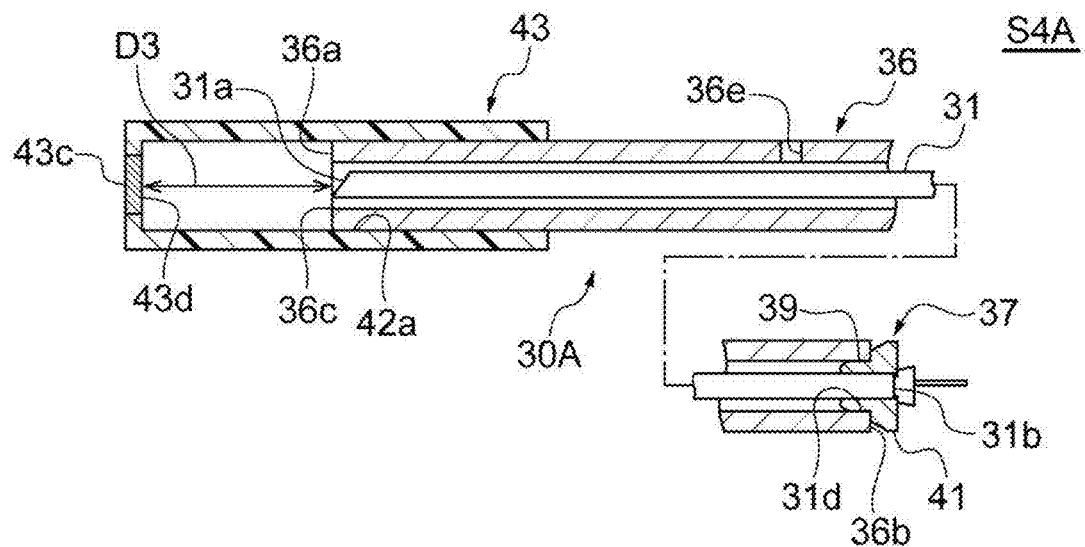
Figure 10:
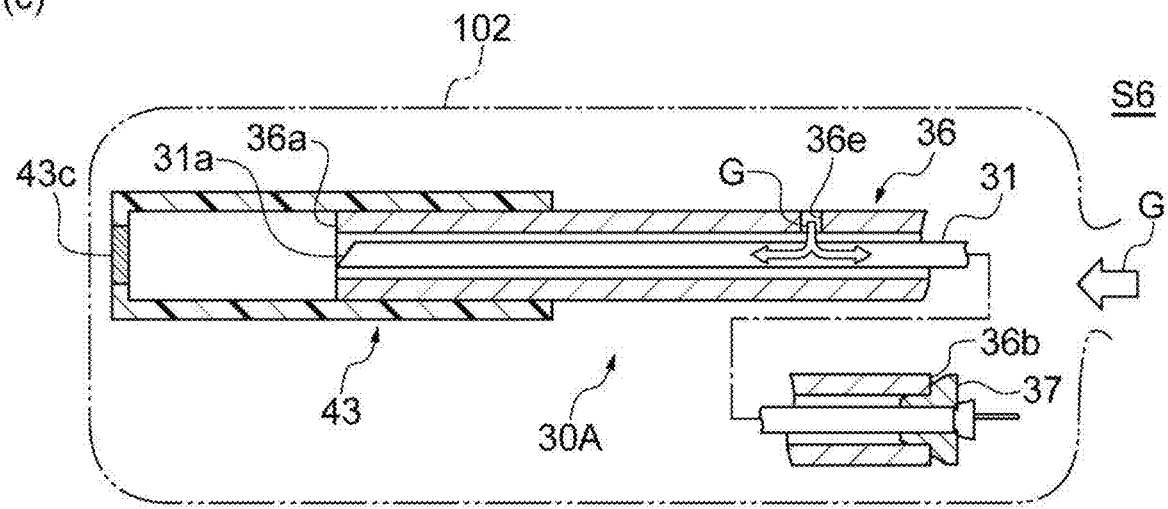

Step S2A is performed (FIG. 10(a)). First, the protection cap 43 is mounted on the hoop 36. In Step S2A, the protection cap 43 is not completely covered on the hoop 36. Specifically, the tip end surface of the hoop tip end portion 36a is not in contact with the inner surface of the cap tip end wall 43d. That is, a predetermined gap D3 is provided between the inner surface of the cap tip end wall 43d and the tip end surface of the hoop tip end portion 36a.

Step S4A is performed (refer to FIG. 10(b)). In Step S4A, the catheter 31 is accommodated in the hoop 36. Here, in Step S2A, the protection cap 43 is mounted on the hoop 36 so that the predetermined distance D3 is provided between the protection cap 43 and the hoop 36. Additionally, in Step S4A, the catheter tip end portion 31a is disposed to coincide with the hoop tip end portion 36a. Then, the predetermined gap D3 is also formed between the catheter tip end portion 31a and the cap tip end wall 43d. Therefore, the catheter tip end portion 31a can be protected because the catheter tip end portion 31a is not in contact with the inner surface of the cap tip end wall 43d. Also, in a procedure of performing Steps S2A and S4A, Step S4A may be performed after Step S2A, as described above. In addition, Step S2A may be performed after Step S4A.

Step S6 is performed (refer to FIG. 10(c)). The specific process is the same as Step S6 according to the first embodiment. Subsequently, Step S8 is performed (refer to FIG. 11(a)). The specific process is the same as Step S8 according to the first embodiment.

Figure 11:
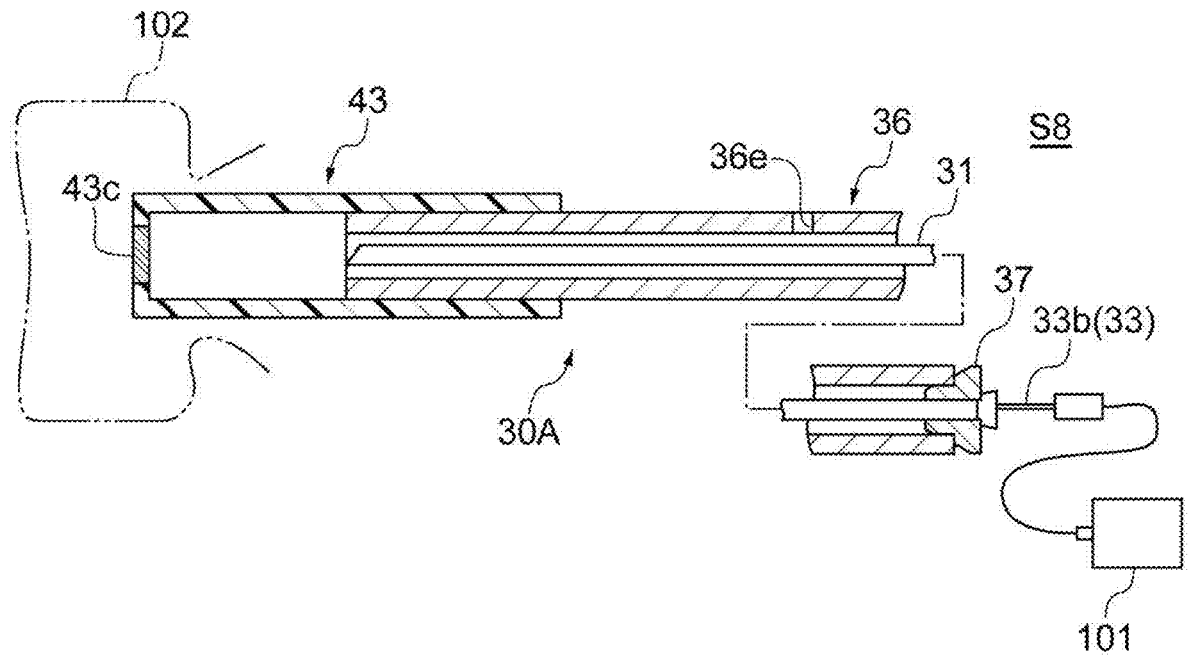
FIG. 11 is a view for explaining a main process following the process shown in FIG. 10.
Figure 11:
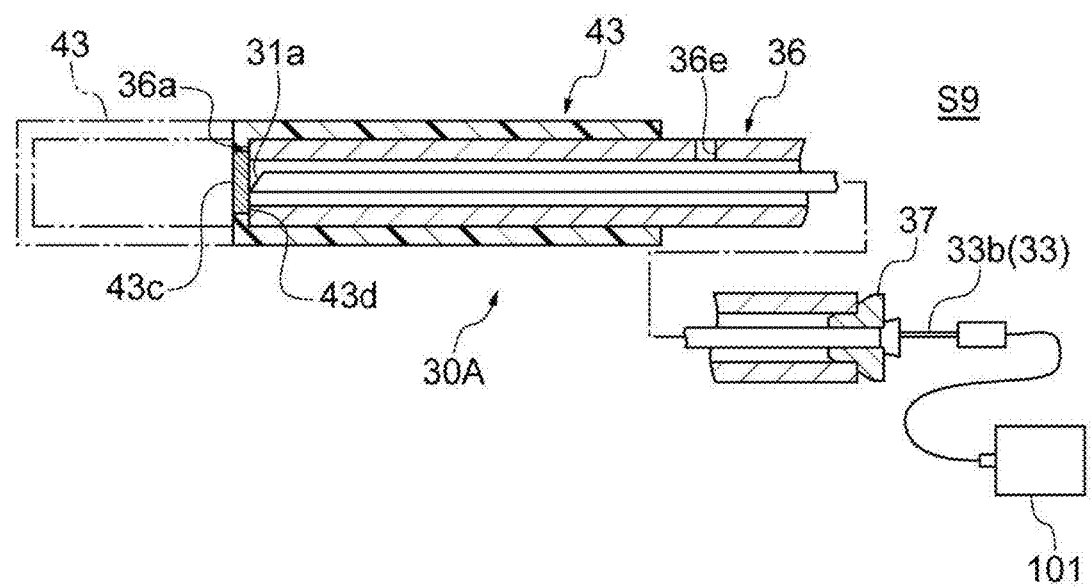

Step S9 is performed (refer to FIG. 11(b)). In Step S9, the protection cap 43 is pushed into the hoop 36 side. As a result, the inner surface of the cap tip end wall 43d is in contact with the tip end surface of the hoop tip end portion 36a. Due to Step S9, the position of the catheter tip end portion 31a coincides with the position of the hoop tip end portion 36a.

Figure 12:
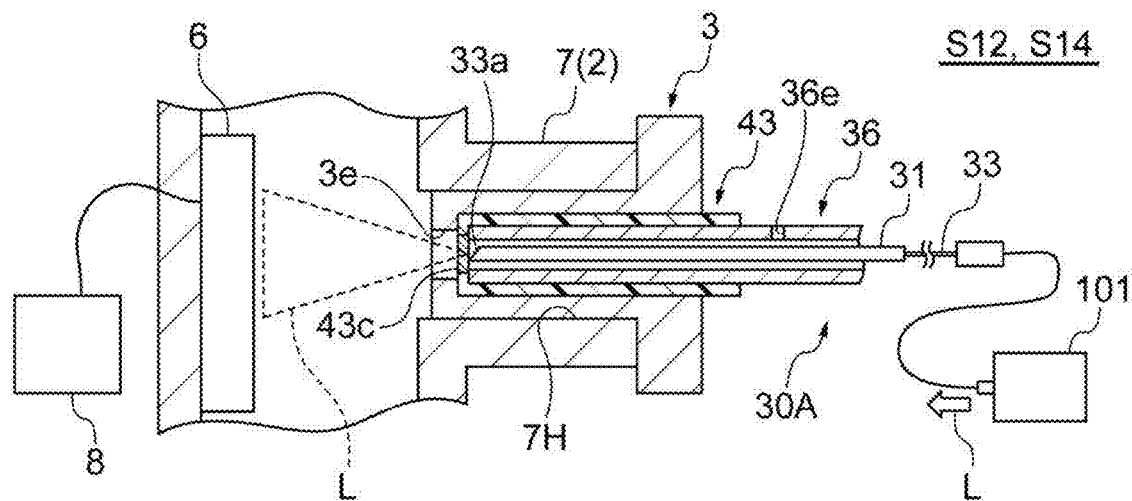
FIG. 12 is a view for explaining a main process following the process shown in FIG. 11.
Figure 12:
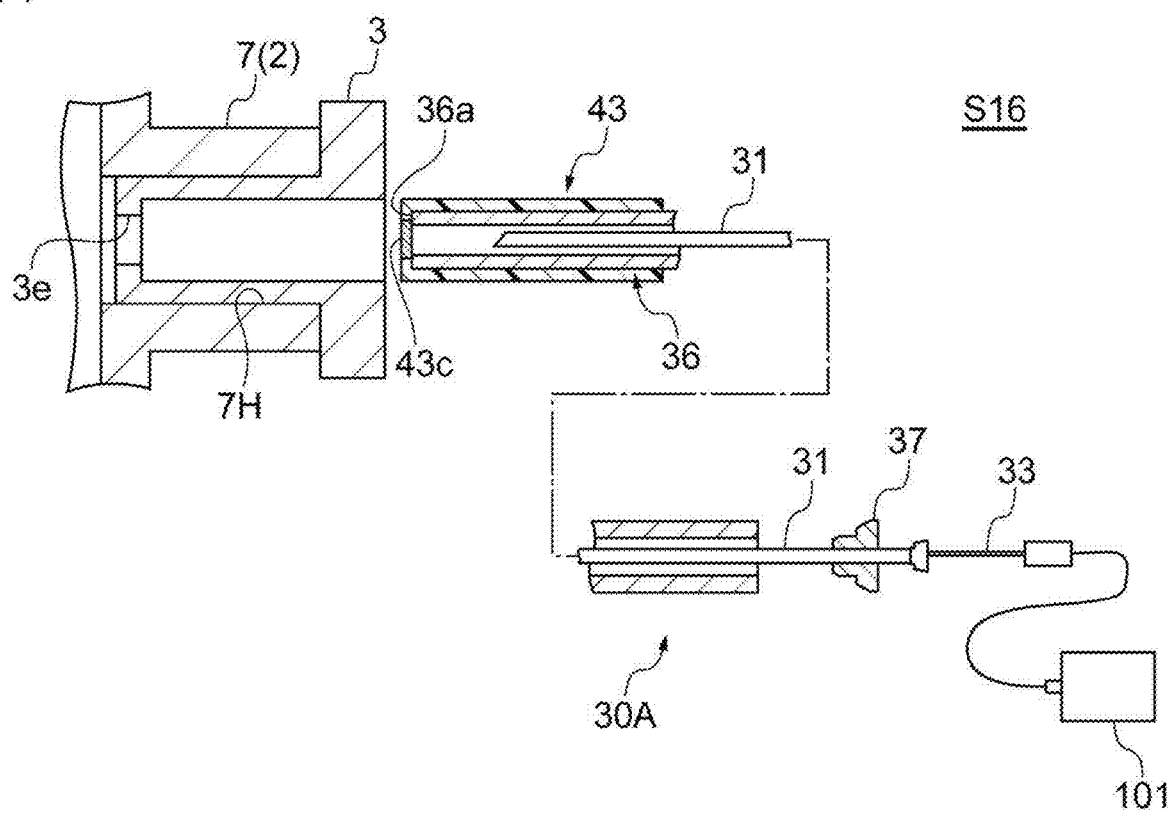

The specific processes thereafter are substantially the same as Steps S12, S14, S16 and S18 according to the first embodiment. That is, the adapter 3 is screwed into the mounting part 7 in Step S12 (refer to FIG. 12(a)). Then, a tip end portion of the catheter kit 30A is inserted into the adapter 3. Subsequently, in Step S14 (refer to FIG. 12(a)), the light source 101 is operated. As a result, the laser light L is generated. The intensity of the laser light L is confirmed. Subsequently, in Step S16 (refer to FIG. 12(b)), the catheter kit 30A is pulled out of the adapter 3. Thereafter, the catheter 31 is pulled out of the hoop 36. Then, in Step S18 (not shown), a predetermined treatment or examination is performed using the catheter 31.

The light measurement method according to the second embodiment can maintain the cleanliness of the catheter 31 as in the light measurement method according to the first embodiment and can easily confirm the light intensity.

The present invention has been described above in detail on the basis of the embodiments. However, the present invention is not limited to the above-described embodiments. The present invention can be variously modified without departing from the scope of the invention. For example, the catheter kit is not limited to the configurations shown in the above-described embodiments. The catheter kit can take a variety of configurations.

The catheter kits 30 and 30A according to the first embodiment and the second embodiment have the configuration (the protection cap 43) which closes the tip end opening 36c of the hoop tip end portion 36a. The configuration which closes the tip end opening 36c may be a configuration shown in the following first, second and third modified examples.

Modified Example 1

Figure 13:
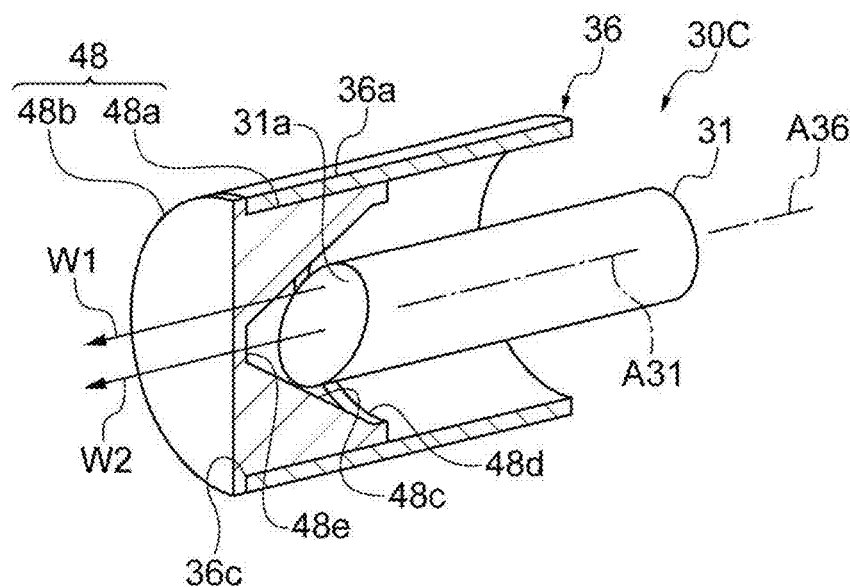
FIG. 13 is a perspective view showing a cross section of a catheter kit according to first, second and third modified examples.
Figure 13:
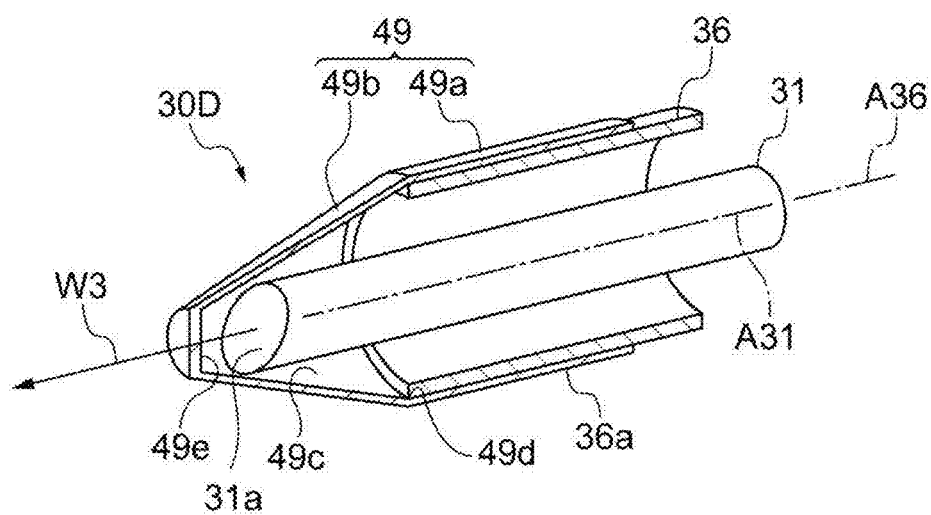
Figure 13:
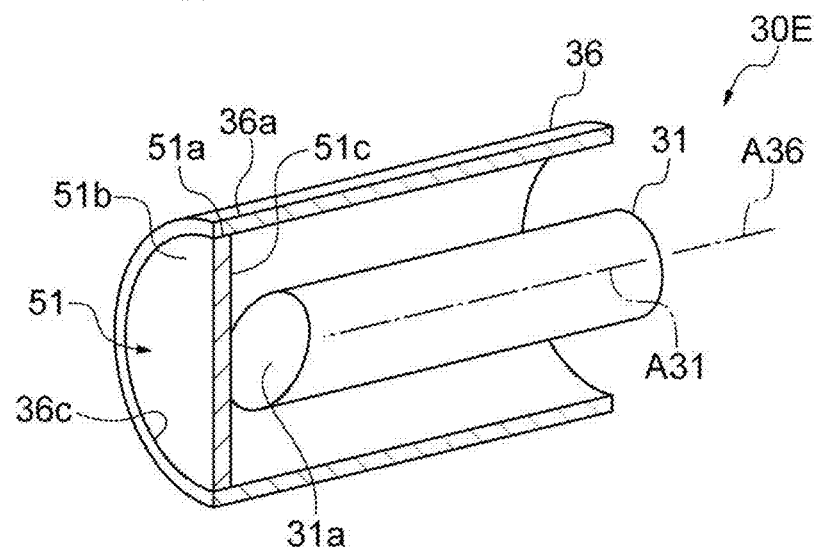

As shown in FIG. 13(a), a catheter kit 30C according to the first modified example has a protection cap 48. The protection cap 48 may be detachable from the hoop 36. Also, the protection cap 48 may be fixed to the hoop 36 by an adhesive or the like so that it cannot be removed from the hoop 36. The protection cap 48 is formed of a material transparent to the laser light L. The protection cap 48 has a cap main body 48a and a flange part 48b. The cap main body

48a has a cylindrical shape. The cap main body 48a is fitted into the hoop tip end portion 36a. The flange part 48b is provided on the tip end side of the cap main body 48a. The flange part 48b has a disk shape. The flange part 48b has a diameter substantially the same as a diameter of the outer circumferential surface of the hoop 36. That is, the diameter of the flange part 48b is larger than an inner diameter of the tip end opening 36c. According to such a configuration, a base end surface of the flange part 48b is in contact with the tip end surface of the hoop tip end portion 36a. As a result, an insertion depth of the protection cap 48 can be defined.

The protection cap 48 has a catheter arrangement part 48c which defines a position of the catheter tip end portion 31a. The catheter arrangement part 48c aligns a central axis A31 of the catheter 31 with a central axis A36 of the hoop 36. In other words, the catheter arrangement part 48c defines the position of the catheter tip end portion 31a in a radial direction of the hoop 36. Furthermore, the catheter arrangement part 48c also defines a direction of the catheter 31 (that is, an emitting direction of the laser light L) in a predetermined direction. According to such a catheter arrangement part 48c, the position and posture of the catheter tip end portion 31a with respect to the light receiving part 6 can be defined with high accuracy. Therefore, it is possible to obtain an accurate light intensity value. In addition, it is possible to curb the occurrence of variations in light intensity for each measurement.

The catheter arrangement part 48c is a tapered hole and extends from a base end surface of the cap main body 48a toward the flange part 48b. A diameter of the catheter arrangement part 48c gradually decreases toward the flange part 48b. The catheter arrangement part 48c has a base end opening 48d provided in a base end surface thereof, and a bottom portion 48e provided on the flange part 48b side. An inner diameter of the base end opening 48d is larger than an outer diameter of the catheter 31. Furthermore, the inner diameter of the base end opening 48d is slightly smaller than the inner diameter of the hoop 36. A diameter of the bottom portion 48e is smaller than the outer diameter of the catheter 31. Therefore, the tip end surface of the catheter tip end portion 31a is not in contact with the bottom portion 48e. According to such a catheter arrangement part 48c, when the catheter 31 is inserted into the hoop 36 from the base end side toward the tip end side, the catheter tip end portion 31a can be suitably guided to the catheter arrangement part 48c. When the protection cap 48 is used, the tip end surface of the catheter tip end portion 31a does not protrude from the tip end surface of the hoop tip end portion 36a. Therefore, the position of the catheter tip end portion 31a in the emitting direction of the laser light L is defined.

According to the protection cap 48, the laser light L passes through the cap main body 48a and the flange part 48b and is incident on the light receiving part 6. Specifically, a shape of the catheter arrangement part 48c may be configured so that an optical axis of the laser light L intersects a tapered surface of the catheter arrangement part 48c (refer to an arrow W1). The shape of the catheter arrangement part 48c may be configured so that the optical axis of the laser light L does not intersect the tapered surface. That is, the shape of the catheter arrangement part 48c may be configured so that the optical axis of the laser light L intersects the bottom portion 48e (refer to an arrow W2).

Modified Example 2

As shown in FIG. 13(b), a catheter kit 30D according to a second modified example can also regulate the position of the catheter tip end portion 31a, like the catheter kit 30C of the first modified example.

The catheter kit 30D has a protection cap 49. The protection cap 49 may be detachable from the hoop 36. The protection cap 49 may be fixed to the hoop 36 by an adhesive or the like so that it cannot be removed from the hoop 36. The protection cap 49 has a main body tubular part 49a and a tapered tubular part 49b. The main body tubular part 49a is a tubular member which covers the hoop tip end portion 36a. An inner diameter of the main body tubular part 49a is substantially the same as or slightly smaller than the outer diameter of the hoop 36. The tapered tubular part 49b is provided on the tip end side of the main body tubular part 49a. The tapered tubular part 49b has a truncated cone shape. An outer diameter of the tapered tubular part 49b gradually decreases from a portion thereof which is continuous with the main body tubular part 49a to the tip end side. The tapered tubular part 49b has a tapered hole. An inner diameter of the tapered hole gradually decreases towards the tip end. The tapered hole is a catheter arrangement part 49c.

The catheter arrangement part 49c is a tapered hole. The tapered hole extends from a boundary between the main body tubular part 49a and the tapered tubular part 49b toward the tip end. The diameter of the catheter arrangement part 49c gradually decreases toward the tip end. The catheter arrangement part 49c has a base end opening 49d and a tip end bottom portion 49e. An inner diameter of the base end opening 49d is substantially the same as the outer diameter of the hoop 36. A diameter of the tip end bottom portion 49e is smaller than the outer diameter of the catheter 31. Therefore, the tip end surface of the catheter tip end portion 31a is not in contact with the tip end bottom portion 49e. According to such a catheter arrangement part 49c, when the catheter 31 is inserted into the hoop 36 from the base end side to the tip end side, the catheter tip end portion 31a can be suitably guided to the catheter arrangement part 49c. Also, when the protection cap 49 is used, the tip end surface of the catheter tip end portion 31a protrudes from the tip end surface of the hoop tip end portion 36a. According to such a configuration, the catheter tip end portion 31a can be brought close to the light receiving part 6 in a state in which the catheter tip end portion 31a is protected.

According to the protection cap 49, the laser light L passes through the tapered tubular part 49b and is incident on the light receiving part 6. Specifically, in a shape of the catheter arrangement part 49c, the optical axis of the laser light L intersects the tip end bottom portion 49e without intersecting the tapered surface (refer to an arrow W3). Also, the shape of the catheter arrangement part 49c may be so that the optical axis of the laser light L intersects the tapered surface.

Modified Example 3

As shown in FIG. 13(c), a catheter kit 30E according to a third modified example has a protection cover part 51. The protection cover part 51 has a disk shape. The protection cover part 51 has an outer circumferential surface 51a, a tip end surface 51b, and a base end surface 51c. An outer diameter of the protection cover part 51 is approximately equal to the inner diameter of the hoop 36. The protection cover part 51 is fitted into the tip end opening 36c of the hoop tip end portion 36a. The tip end surface 51b of the protection cover part 51 is exposed to the outside. The base end surface 51c of the protection cover part 51 faces the inside of the hoop 36. That is, the catheter tip end portion 31a faces the base end surface 51c. The laser light L emitted from the catheter tip end portion 31a passes through the protection cover part 51 and is then incident on the light receiving part 6. Therefore, the protection cover part 51 is formed of a material transparent to the laser light L.

The protection cover part 51 is fixed to the hoop 36 by an adhesive or the like so that it cannot be removable therefrom. That is, the protection cover part 51 is integrated with the hoop 36. Specifically, the outer circumferential surface 51a of the protection cover part 51 is fixed to the inner circumferential surface of the hoop 36 by adhesion or the like. According to such a configuration, the protection cover part 51 is not separated from the hoop 36. Therefore, the catheter tip end portion 31a can be reliably protected.

The catheter kit 30 according to the first embodiment has included the position adjustment mechanism 47 which switches the position of the catheter 31 with respect to the hoop 36. The specific configuration of the position adjustment mechanism may be as shown in the following fourth and fifth modified examples.

Modified Example 4

Figure 14:
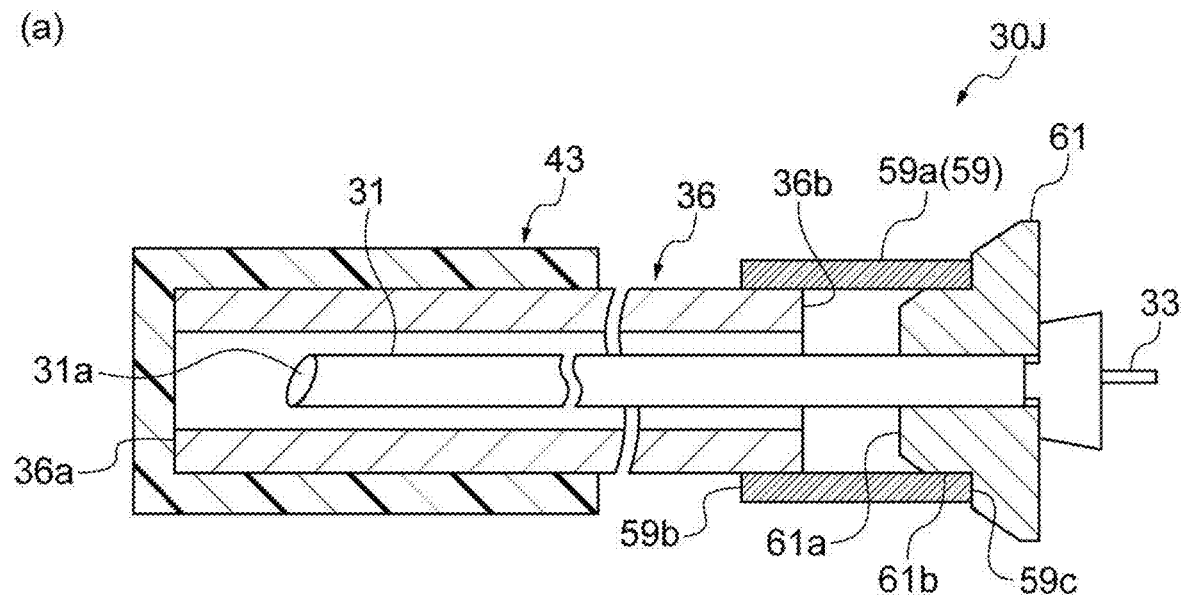
FIG. 14 is a side view showing a cross section of a catheter kit according to a fourth modified example.
Figure 14:
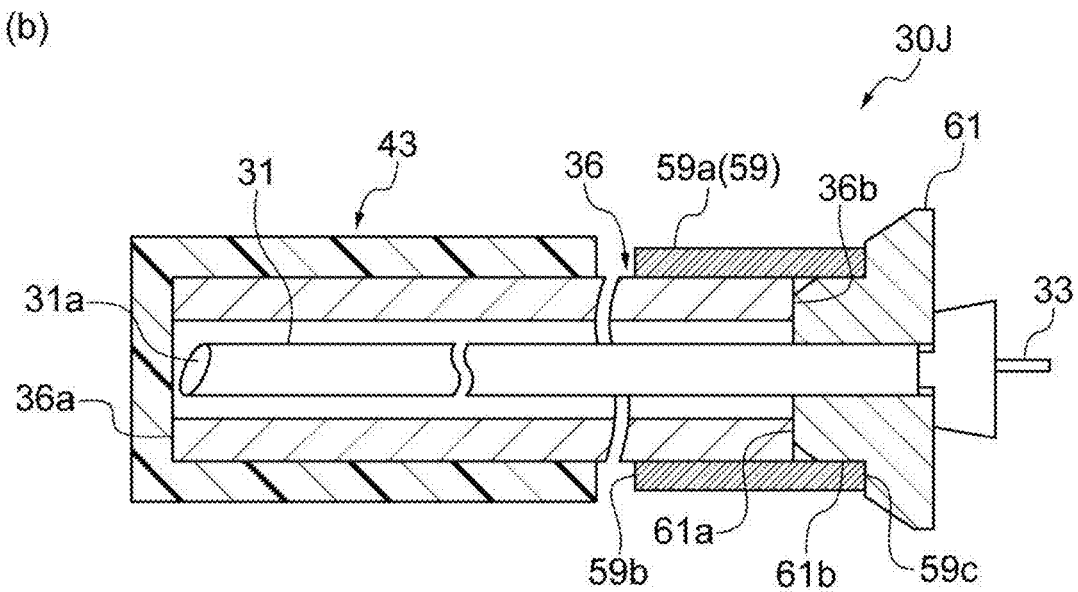

As shown in FIG. 14, a catheter kit 30J according to a fourth modified example has a position adjustment mechanism 59 which has a different structure from that in the third embodiment. The position adjustment mechanism 59 is a tube 59a formed of silicone rubber or the like. The tube 59a is disposed between the hoop 36 and the holding plug 61. The tube 59a maintains and changes a gap between the hoop base end portion 36b and a holding plug tip end surface 61a.

The hoop base end portion 36b is inserted into a tube tip end portion 59b. A press-fit part 61b of the holding plug 61 is inserted into a tube base end portion 59c. In other words, the position adjustment mechanism 59 is a double structure configured with the tube 59a and the hoop 36. Here, the tube base end portion 59c is fixed to the holding plug 61. On the other hand, the tube tip end portion 59b is slidable with respect to the hoop base end portion 36b. Such a configuration can be realized by setting an inner diameter of the tube tip end portion 59b and an outer diameter of the hoop base end portion 36b to predetermined dimensional values.

As shown in FIG. 14(a), when the catheter kit 30J is stored or the like, the tube 59a maintains a gap between the hoop base end portion 36b and the holding plug tip end surface 61a at a predetermined distance. At this time, the catheter tip end portion 31a is disposed on the base end side by a gap with respect to the hoop tip end portion 36a (the first position). That is, the catheter tip end portion 31a is protected by the hoop 36.

As shown in FIG. 14(b), when the measurement of the laser light L is performed using the catheter kit 30J, the holding plug 61 is pushed to the tip end side. Then, slippage occurs between the tube tip end portion 59b and the hoop base end portion 36b. As a result, the tube 59a and the holding plug 61 move integrally to the tip end side. That is, the gap between the hoop base end portion 36b and the holding plug tip end surface 61a is reduced. Then, finally, the holding plug tip end surface 61a comes into contact with the hoop base end portion 36b. At this time, the catheter tip end portion 31a coincides with the position of the hoop tip end portion 36a. That is, the catheter tip end portion 31a is disposed at a position (the second position) suitable for measurement of the light intensity.

Modified Example 5

Figure 15:
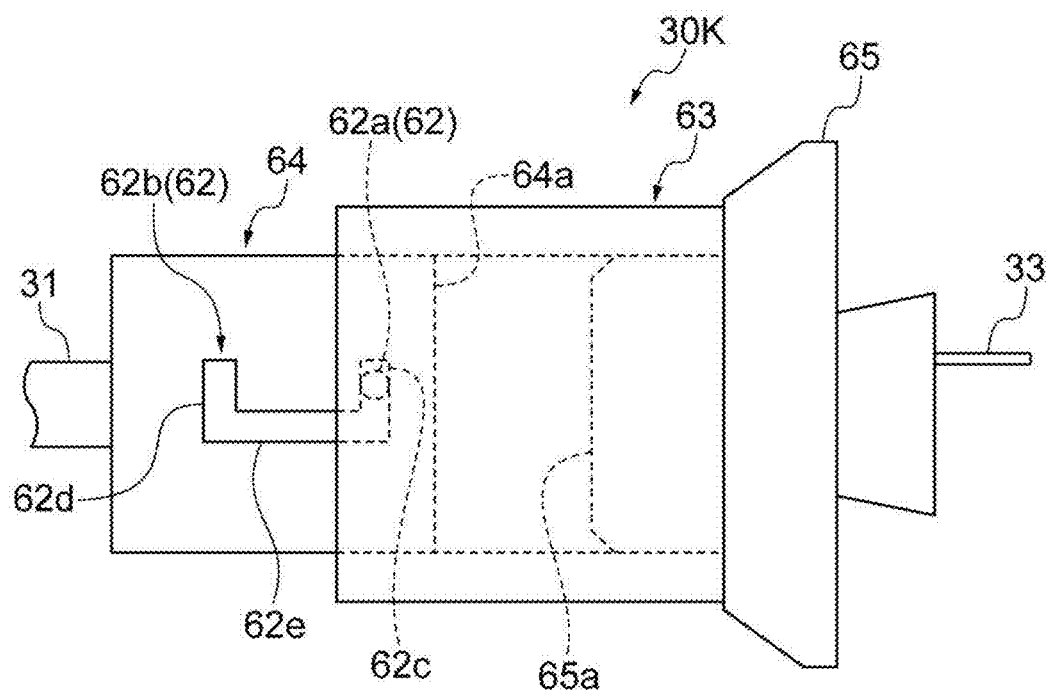
FIG. 15 is a plan view showing a catheter kit according to a fifth modified example.
Figure 15:
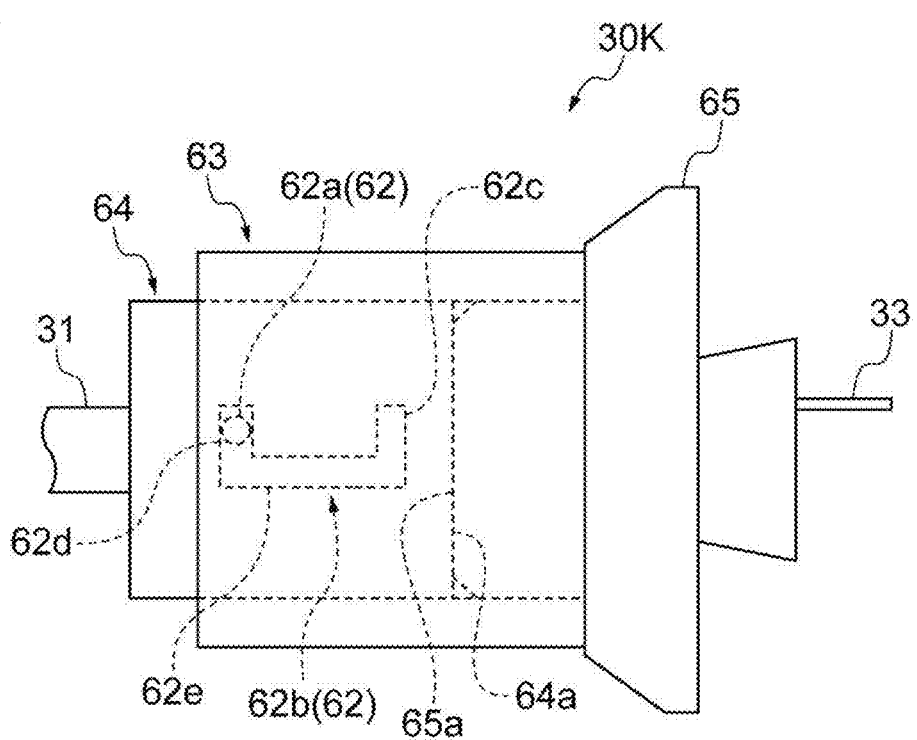

As shown in FIG. 15, a catheter kit 30K according to a fifth modified example may have a position adjustment mechanism 62 having yet another configuration. The position adjustment mechanism 62 is configured with a guide pin 62a and a guide groove 62b. The guide pin 62a and the guide groove 62b reliably switch between a state in which the catheter tip end portion 31a is protected and a state in which the measurement of the laser light L is performed using the catheter kit 30K. Furthermore, the position adjustment mechanism 62 can reliably maintain each of the states. The catheter kit 30K has a tube 63. The tube 63 is disposed between the hoop 64 and the holding plug 65. That is, like the position adjustment mechanism 62 according to the fourth modified example, the position adjustment mechanism 62 according to the fifth modified example has a so-called double structure.

For example, the guide groove 62b is provided in the outer circumferential surface of the hoop base end portion 64a. The guide groove 62b may penetrate the side wall of the hoop 64. Also, the guide groove 62b may have a bottom portion. The guide groove 62b includes a first restricting part 62c and a second restricting part 62d which extend in a circumferential direction, and a connecting groove part 62e which extends in an axial direction. One end of the first restricting part 62c and one end of the second restricting part 62d are connected by the connecting groove part 62e. The connecting groove part 62e extends in the axial direction of the hoop 64. The first restricting part 62c is provided on the hoop base end surface side. The second restricting part 62d is provided on the tip end side from the first restricting part 62c. A distance from the first restricting part 62c to the second restricting part 62d corresponds to a movement distance of the catheter 31. The guide pin 62a is provided on an inner circumferential surface of the tube 63. The guide pin 62a is a cylindrical protrusion. The guide pin 62a extends from the inner circumferential surface of the tube 63 in the radial direction thereof. A diameter of the guide pin 62a is substantially the same as or slightly smaller than that of the guide groove 62b.

As shown in FIG. 15(a), when the catheter kit 30K is stored or the like, the guide pin 62a is fitted into the first restricting part 62c. When the guide pin 62a is fitted into the first restricting part 62c, the catheter tip end portion 31a is in a protected state in which it is disposed on the inner side of the hoop 64 (at the first position). The first restricting part 62c extends in the circumferential direction. As a result, the guide pin 62a does not move in the axial direction. Therefore, since the catheter tip end portion 31a is disposed at the inside of the hoop 64, the protected state can be reliably maintained.

Next, a switching operation will be described. As shown in FIG. 15(b), first, the tube 63 is rotated in a direction in which the first restricting part 62c extends. Then, the guide pin 62a moves to the base end of the connecting groove part 62e. Then, the guide pin 62a is moved along the connecting groove part 62e. That is, the tube 63 and the holding plug 65 are moved to the tip end side. Due to this movement, the catheter tip end portion 31a coincides with the hoop tip end portion 36a. Then, after the guide pin 62a is moved to the tip end of the connecting groove part 62e, the tube 63 is rotated in the circumferential direction. Then, the guide pin 62a is fitted into the second restricting part 62d. When the guide pin 62a is fitted into the second restricting part 62d, the catheter tip end portion 31a is in a measurement state in which it coincides with the hoop tip end portion 36a (the second position). The second restricting part 62d extends in the circumferential direction, like the first restricting part 62c. As a result, the guide pin 62a does not move in the axial direction. Therefore, a state in which the catheter tip end portion 31a is disposed at the hoop tip end portion 36a can be reliably maintained.

The catheter kit 30 according to the first embodiment has the mechanism for holding the position of the catheter 31 with respect to the hoop 36. The specific configuration of the mechanism may be as shown in the following sixth, seventh and eighth modified examples.

Modified Example 6

Figure 16:
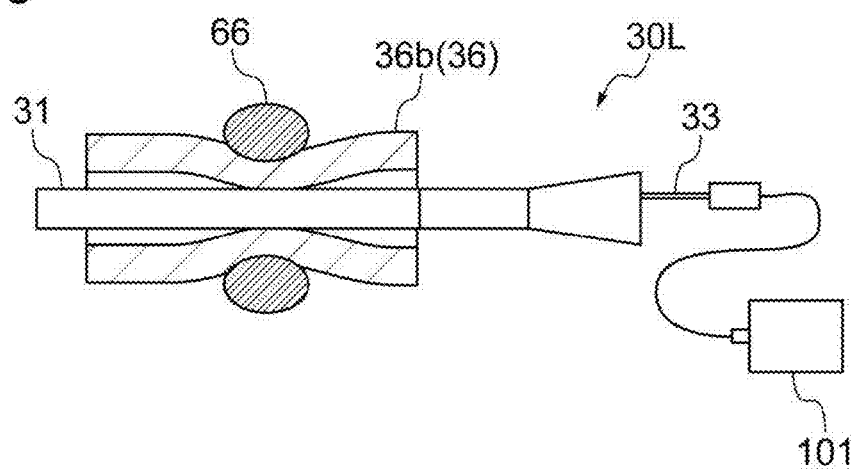
FIG. 16 is a side view showing a cross section of a catheter kit according to sixth, seventh and eighth modified examples.
Figure 16:
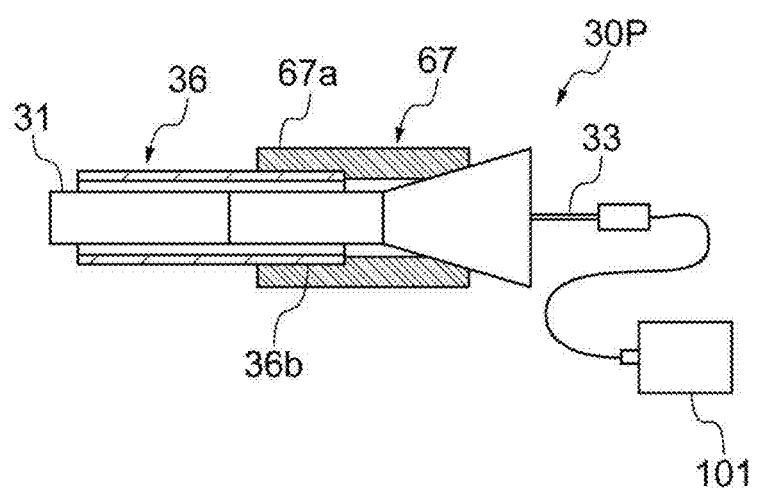
Figure 16:
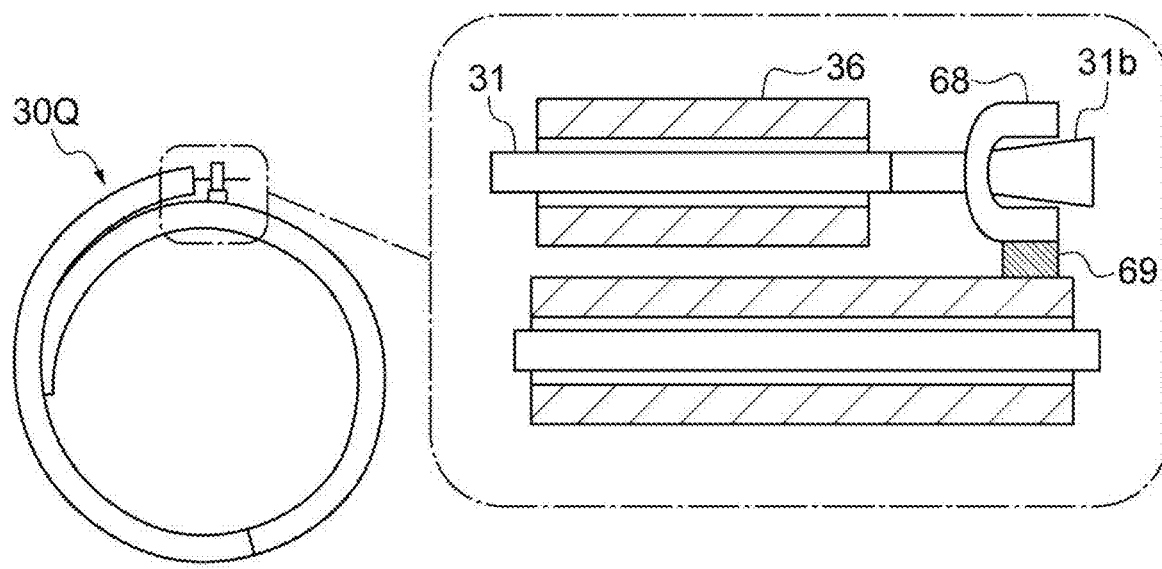

As shown in FIG. 16(a), a catheter kit 30L according to a sixth modified example may have a clip 66 as the mechanism for holding the position of the catheter 31. The clip 66 is mounted on the hoop base end portion 36b. The clip 66 generates a force as if it crushes the hoop 36 in the radial direction. When the hoop 36 is crushed in the radial direction, the inner circumferential surface of the hoop 36 is in tight contact with the outer circumferential surface of the catheter 31. The clip 66 is mounted to sandwich the hoop 36 in the radial direction. Therefore, side walls of the hoop 36 crushed by the clip 66 sandwich the catheter 31. According to such a configuration, the position of the catheter 31 with respect to the hoop 36 is maintained. Also, when the hoop 36 is moved, the clip 66 is removed. According to the holding mechanism by the clip 66, it is possible to easily switch between a state in which the catheter 31 is held and a state in which the catheter can be moved.

Modified Example 7

As shown in FIG. 16(b), a catheter kit 30P according to a seventh modified example may have a tube 67 as the holding mechanism. The configuration is similar to the configuration of the fourth modified example. That is, it has a double structure. The difference from the configuration of the fourth modified example is that it is difficult for the tube tip end portion 67a to slide with respect to the hoop base end portion 36b. In the seventh modified example, the inner diameter of the tube 63 is smaller than the outer diameter of the hoop 36. As a result, when the hoop 36 is inserted into the tube 63, a press-fit state is obtained.

Modified Example 8

As shown in FIG. 16(c), a catheter kit 30Q according to an eighth modified example may have a clamp 68 as the holding mechanism. The clamp 68 is a U-shaped component capable of detachably mounting the catheter base end portion 31b. The clamp 68 includes a fixing part 69 which is fixed to the outer circumferential surface of the hoop 36. The catheter base end portion 31b is inserted from an opening of the clamp 68 in the radial direction. As a result, the catheter base end portion 31b is fixed to the clamp 68. The clamp 68 is then fixed to the hoop 36 by the fixing part 69. Thus, the catheter 31 is held with respect to the hoop 36.

The catheter kit 30 according to the first embodiment has the protection cap 48 which is mounted on the hoop tip end portion 36a at the time of storage. The configuration for protecting the catheter tip end portion 31a disposed to coincide with the hoop tip end portion 36a may be configured as shown in the following modified example 9.

Modified Example 9

As shown in FIGS. 17(a) and 17(b), a catheter kit 30S according to a ninth modified example has a protection cap 72. The protection cap 72 has a configuration similar to that of the protection cap 72 of the second modified example. The difference from the protection cap 49 of the second modified example is that the protection cap 72 according to the twelfth modified example can be moved with respect to the hoop 36.

As shown in FIG. 17(a), when the catheter kit 30S is stored, the protection cap 72 is shallowly covered on the hoop tip end portion 36a. According to such a configuration, a space is provided between the cap tip end portion 72a of the protection cap 72 and the catheter tip end portion 31a. Therefore, the catheter tip end portion 31a can be appropriately protected.

On the other hand, as shown in FIG. 17(b), when the measurement of the laser light L using the catheter kit 30S is performed, the protection cap 72 is pushed to the hoop 36 side. A distance between a cap tip end portion 72a and the catheter tip end portion 31a is reduced by the pushing. Then, when the protection cap 72 and the hoop 36 are regarded as one hoop member, the protection cap 72 changes a relative position between the catheter tip end portion 31a and the hoop member. Accordingly, the protection cap 72 may be defined as a broad position adjustment mechanism. Furthermore, the catheter tip end portion 31a is guided along a tapered inner circumferential surface of the protection cap 72. As a result of this guidance, the central axis A31 of the catheter 31 follows the central axis A36 of the hoop 36. Therefore, the variations in the position and posture of the catheter tip end portion 31a from which the laser light L is emitted are curbed. As a result, accurate measurement of light intensity can be performed.

Also, the catheter kit may be freely combined with the first, second, third and ninth modified examples of the tip end shape, the fourth and fifth modified examples of the position adjustment mechanism, and the sixth, seventh and eighth modified examples of the holding mechanism according to conditions required for the catheter kit.

REFERENCE SIGNS LIST

1 Light measurement device
2 Power meter
3 Adapter
3b Adapter base end surface
3H Hoop arrangement part
3Hb Base end opening
4 Case body
6 Light receiving part
7 Mounting part
7a Standing tubular part
7b Mounting end surface
7H Adapter arrangement part
7Ha Tip end opening
7Hb Base end opening
8 Processing device
9 Adapter main body
11 Adapter flange
30, 30A, 30, 30C, 30D, 30E, 30J, 30K, 30L, 30P, 30Q, 30S Catheter kit
31 Catheter
31a Catheter tip end portion
31b Catheter base end portion
32 Catheter accommodating tool
33 Optical fiber
33a Optical fiber tip end portion
33b Optical fiber base end portion
34 Component 36 Hoop
36a Hoop tip end portion
36b Hoop base end portion
36c Tip end opening
36d Base end opening
36e Gas introduction hole
37 Holding plug
38 Catheter arrangement part
39 Press-fit part
41 Flange part
43 Protection cap
43a Cap tip end portion
43b Cap base end portion
43d Cap tip end wall
43c Transmission window
43H Hoop arrangement part
43Hb Base end opening
46 Bellows
46a Bellows tip end portion
46b Bellows base end portion
47 Position adjustment mechanism
48 Protection cap
48a Cap main body
48b Flange part
48c Catheter arrangement part
48d Base end opening
48e Bottom portion
49 Protection cap
49a Main body tubular part
49b Tapered tubular part
49c Catheter arrangement part
49d Base end opening
49e Tip end bottom portion
51 Protection cover part
51a Outer circumferential surface
51b Tip end surface
51c Base end surface
59 Position adjustment mechanism
59a Tube
59b Tube tip end portion
59c Tube base end portion
61 Holding plug
61a Holding plug tip end surface
61b Press-fit part
62 Position adjustment mechanism
62a Guide pin
62b Guide groove
62c First restricting part
62d Second restricting part
62e Connecting groove part
63 Tube
64 Hoop
64a Hoop base end portion
65 Holding plug
66 Clip
67 Tube
67a Tube tip end portion
68 Clamp
69 Fixing part
72 Protection cap
72a Cap tip end portion
102 Sterilization bag
101 Light source
L Laser light
G Sterilization gas

The invention claimed is:

1. A catheter kit comprising:
a catheter having an optical fiber; and
a catheter accommodating tool which accommodates the catheter,
wherein the catheter accommodating tool includes a tubular hoop, a closing part provided at one end of the hoop, and a holding plug detachably attached to the hoop,
the closing part has a transmission window configured to transmit light emitted from the catheter,
the hoop includes a hoop tip end portion at the one end of the hoop at which the closing part is provided, and a hoop base end portion on an opposite side from the hoop tip end portion,
the holding plug includes a press fit part configured to be press-fitted into a base end opening of the hoop base end portion, a catheter arrangement part being a through hole holding the catheter, and a flange part having an outer diameter larger than an inner diameter of the hoop, and
the catheter accommodating tool further includes a bellows disposed between an end surface of the hoop base end portion and the flange part of the holding plug, the bellows being configured to extend and contract in an axial direction of the hoop.

2. The catheter kit according to claim 1, wherein:
the hoop tip end portion of the hoop has an opening, a catheter tip end portion from which light transmitted through the optical fiber is emitted is provided at the hoop tip end portion of the hoop, and
the transmission window is configured to close the opening and transmit the light.

3. The catheter kit according to claim 1, wherein the closing part is a cap member which is detachably mounted on the hoop.

4. The catheter kit according to claim 1, wherein the closing part is a cover part which is a part of the hoop and is integrated with the hoop.

5. The catheter kit according to claim 1, wherein the hoop has a through hole which extends in a direction intersecting a longitudinal direction of the hoop and extends from an outer circumferential surface to an inner circumferential surface.

6. The catheter kit according to claim 1, wherein:
the catheter accommodating tool further includes a position adjustment part provided at the hoop base end portion of the hoop, and
the position adjustment part is configured to change a position of the catheter tip end portion from which the light transmitted through the optical fiber with respect to the hoop tip end portion is emitted.

7. The catheter kit according to claim 1, wherein when the holding plug is attached to the hoop, the press fit part is press-fitted into the base end opening of the hoop base end portion, and the flange part is in contact with the end surface of the hoop base end portion.

* * * * *